(12) United States Patent
Wang et al.

(10) Patent No.: US 8,603,764 B2
(45) Date of Patent: Dec. 10, 2013

(54) EPHA KINASE CANCER DIAGNOSTIC

(75) Inventors: Bingcheng Wang, Solon, OH (US); Hui Miao, Rocky River, OH (US)

(73) Assignee: Case Western Reserve University, Cleveland, OH (US)

( * ) Notice: Subject to any disclaimer, the term of this patent is extended or adjusted under 35 U.S.C. 154(b) by 477 days.

(21) Appl. No.: 12/795,142

(22) Filed: Jun. 7, 2010

(65) Prior Publication Data
US 2011/0027801 A1 Feb. 3, 2011

Related U.S. Application Data

(60) Provisional application No. 61/184,433, filed on Jun. 5, 2009.

(51) Int. Cl.
*G01N 33/574* (2006.01)

(52) U.S. Cl.
USPC .......................................... 435/7.23; 435/7.1

(58) Field of Classification Search
None
See application file for complete search history.

(56) References Cited

PUBLICATIONS

Miao et al, Cancer Cell, 2009, 16:9-20.*
Tockman et al, Cancer Res., 1992, 52:2711s-2718s.*

* cited by examiner

*Primary Examiner* — Mark Halvorson
(74) *Attorney, Agent, or Firm* — Tarolli, Sundheim, Covell & Tummino LLP

(57) ABSTRACT

A method of detecting malignant progression of neoplastic cells in an animal includes obtaining a sample of neoplastic cells from the animal, determining a level of S897-EphA2 phosphorylation in the neoplastic cells of the samplem, and comparing the determined level of S897-EphA2 phosphorylation in the sample to a control value, wherein an increased level of S897-EphA2 phosphorylation compared to the control value is indicative of malignant progression of the neoplastic cell in the animal.

7 Claims, 25 Drawing Sheets

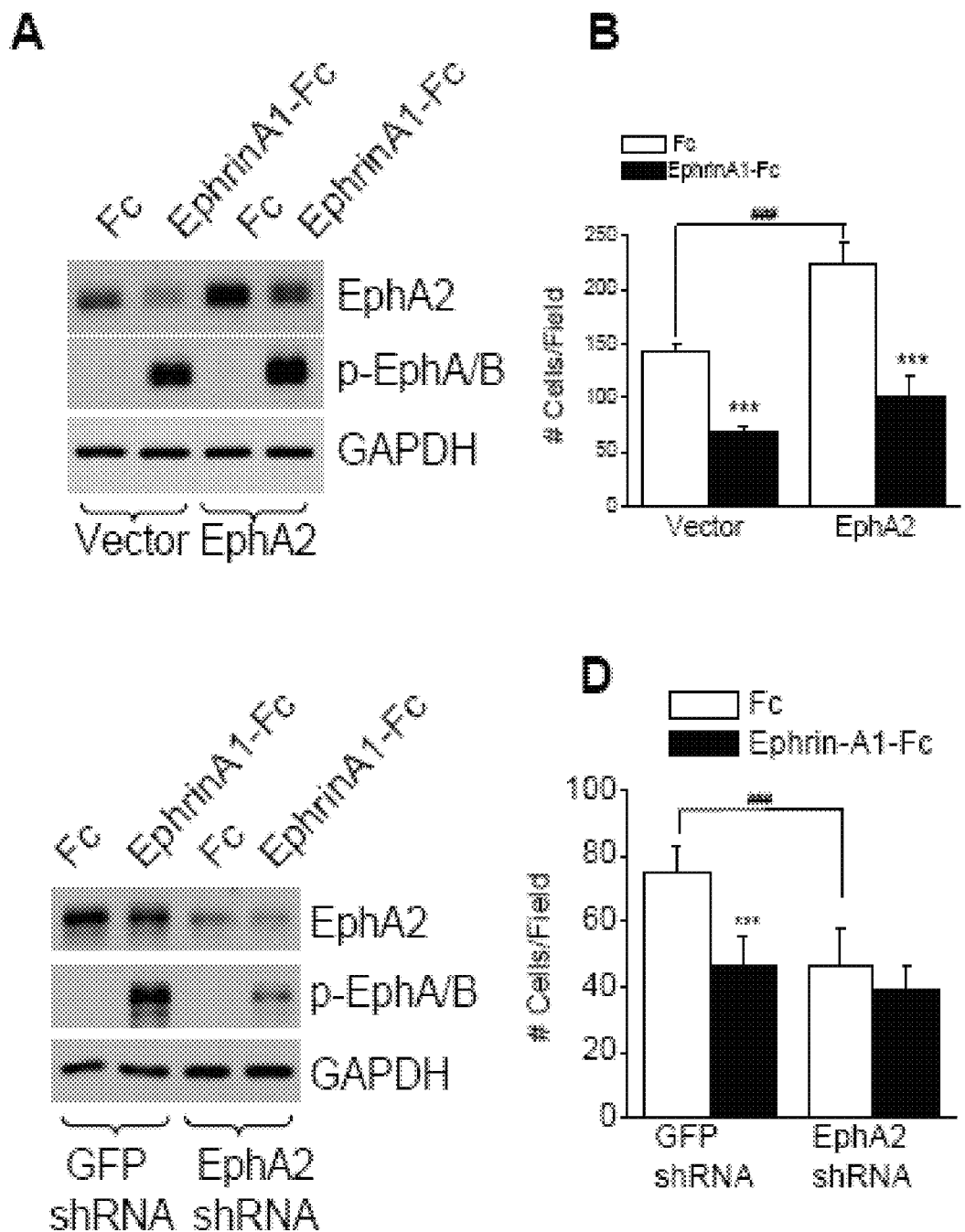
Fig. 1A-D

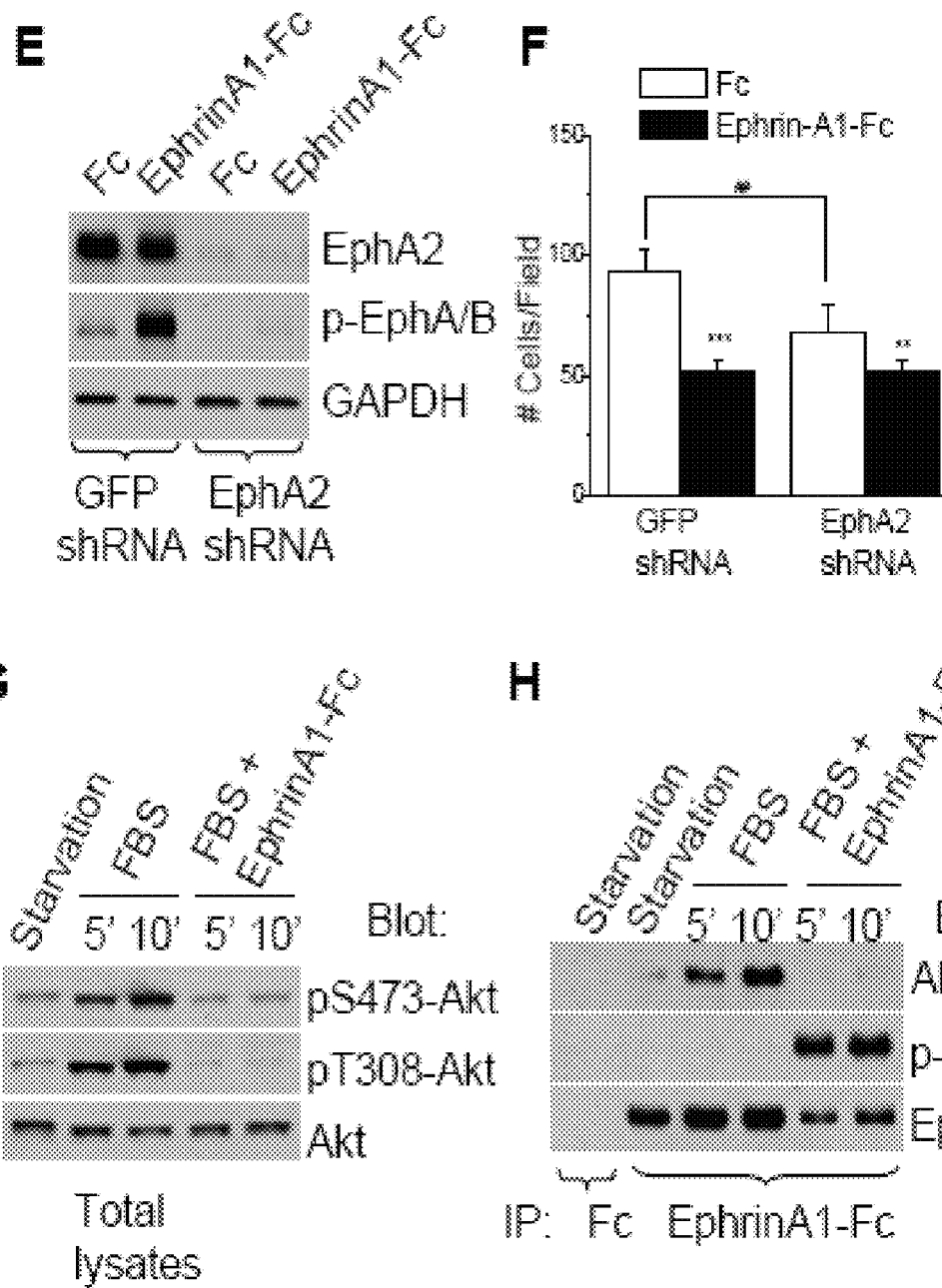
Fig. 1E-H

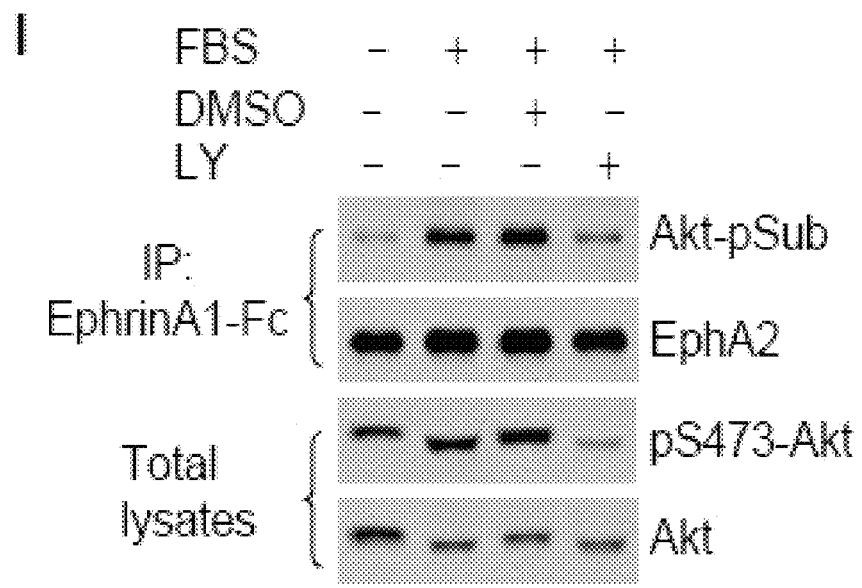
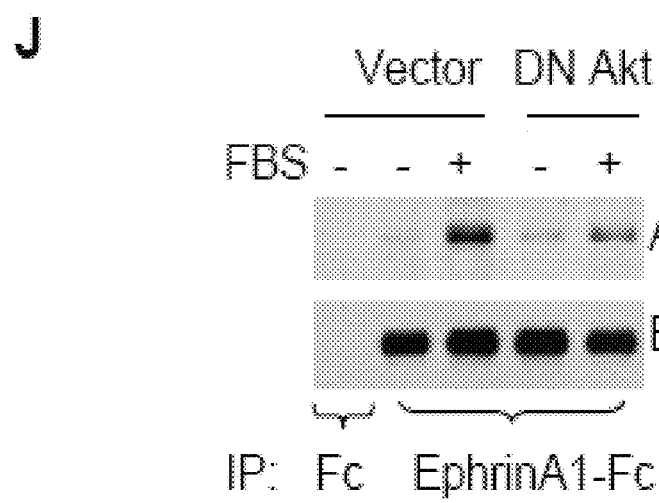
Fig. 1I-J

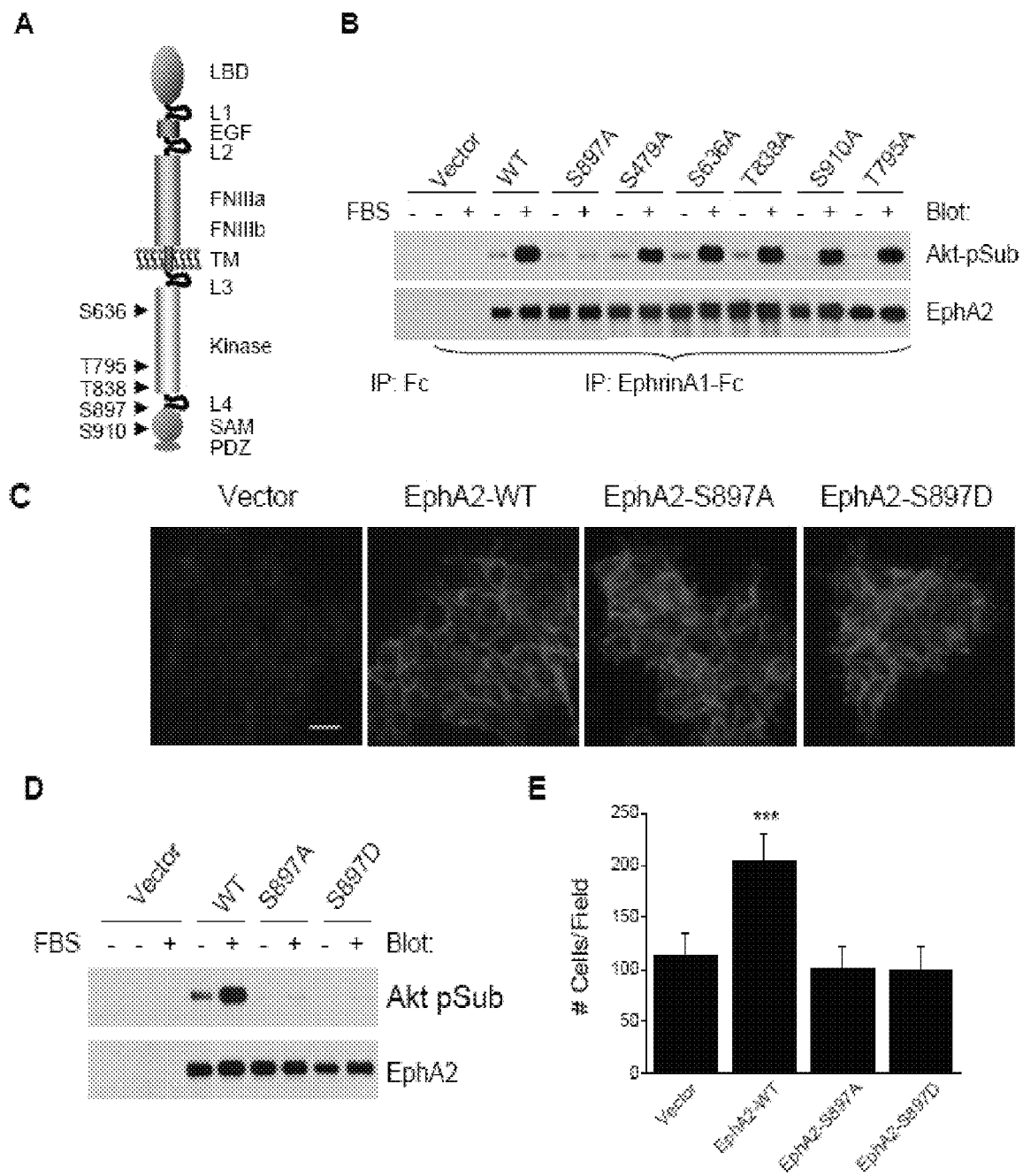
Fig. 2A-E

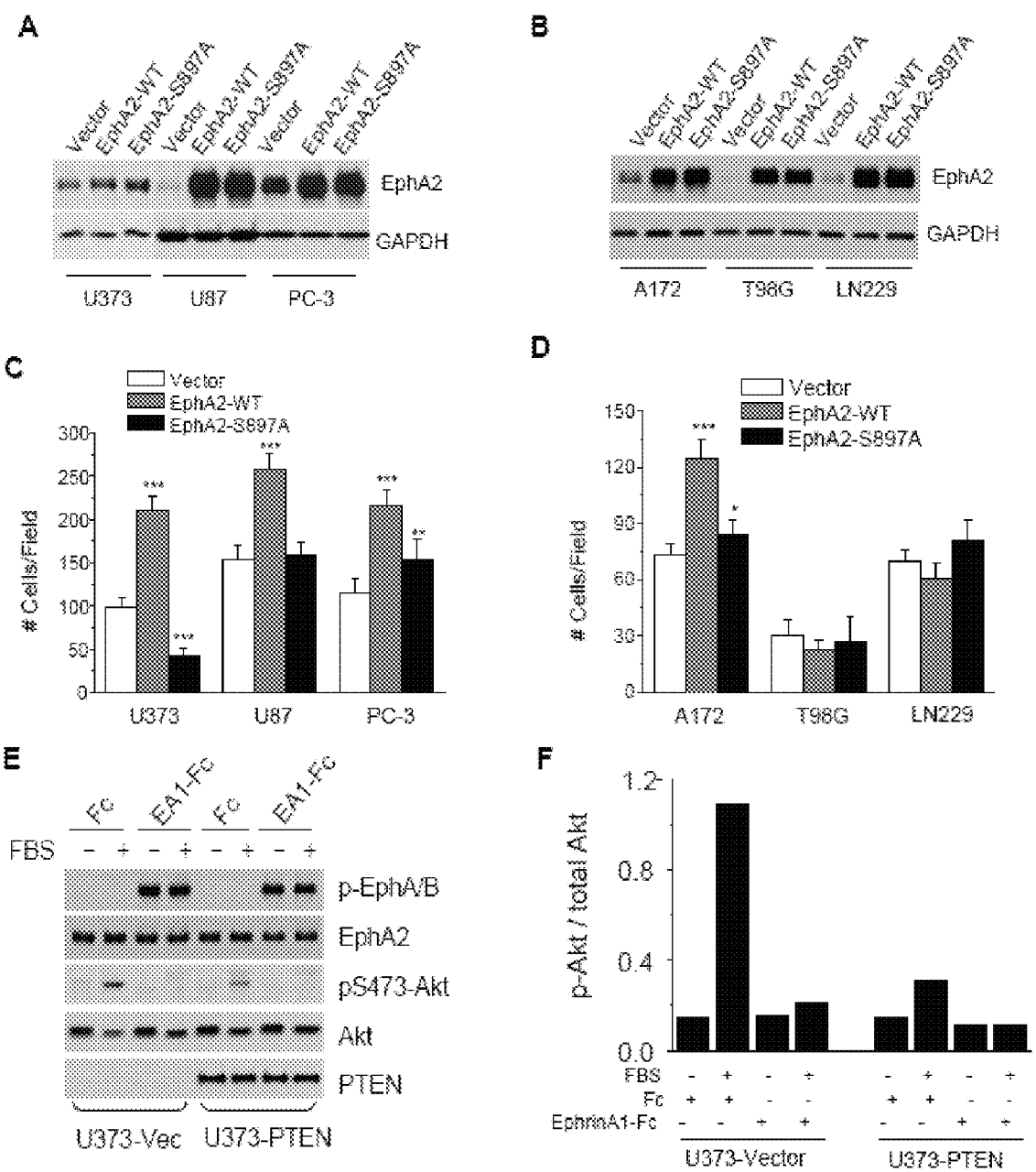
Fig. 3A-F

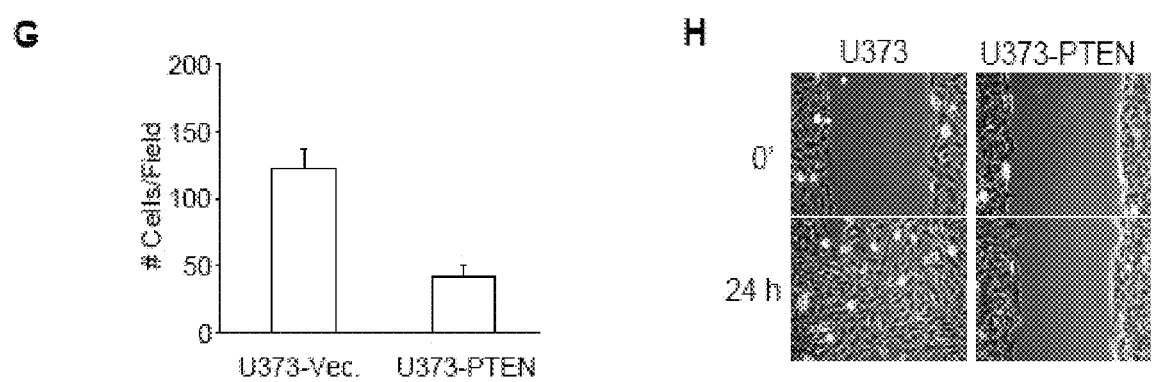
Fig. 3G-H

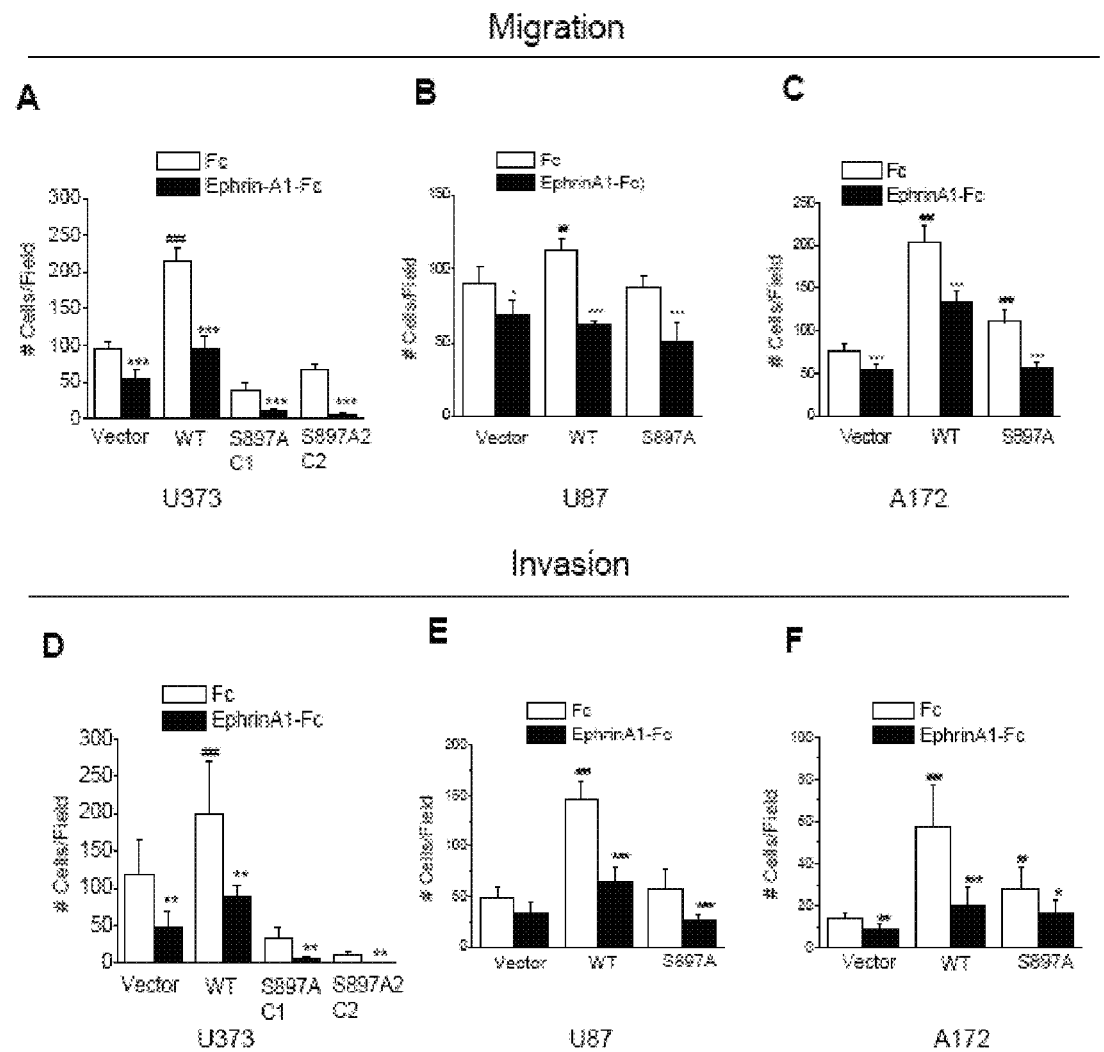
Fig. 4A-F

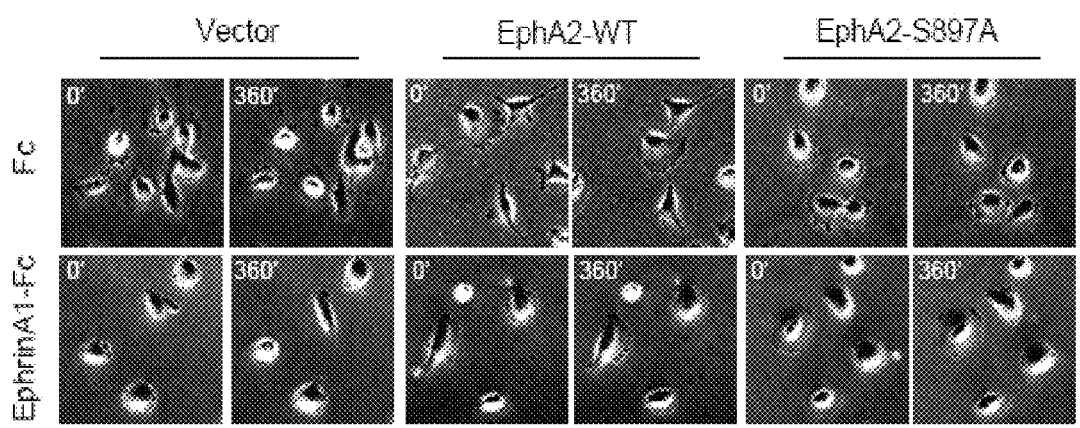
Fig. 4G-
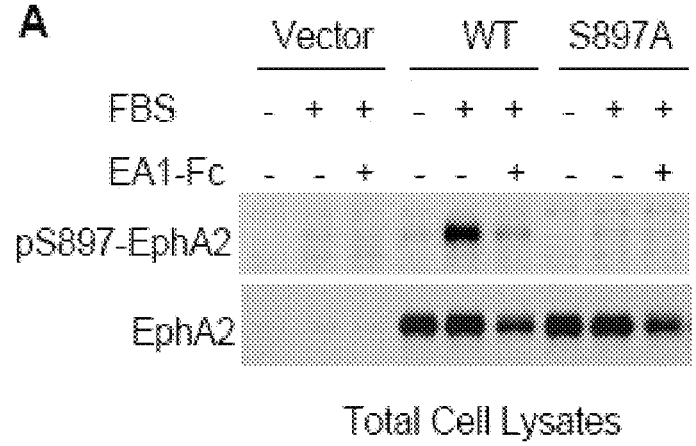
Fig. 5A

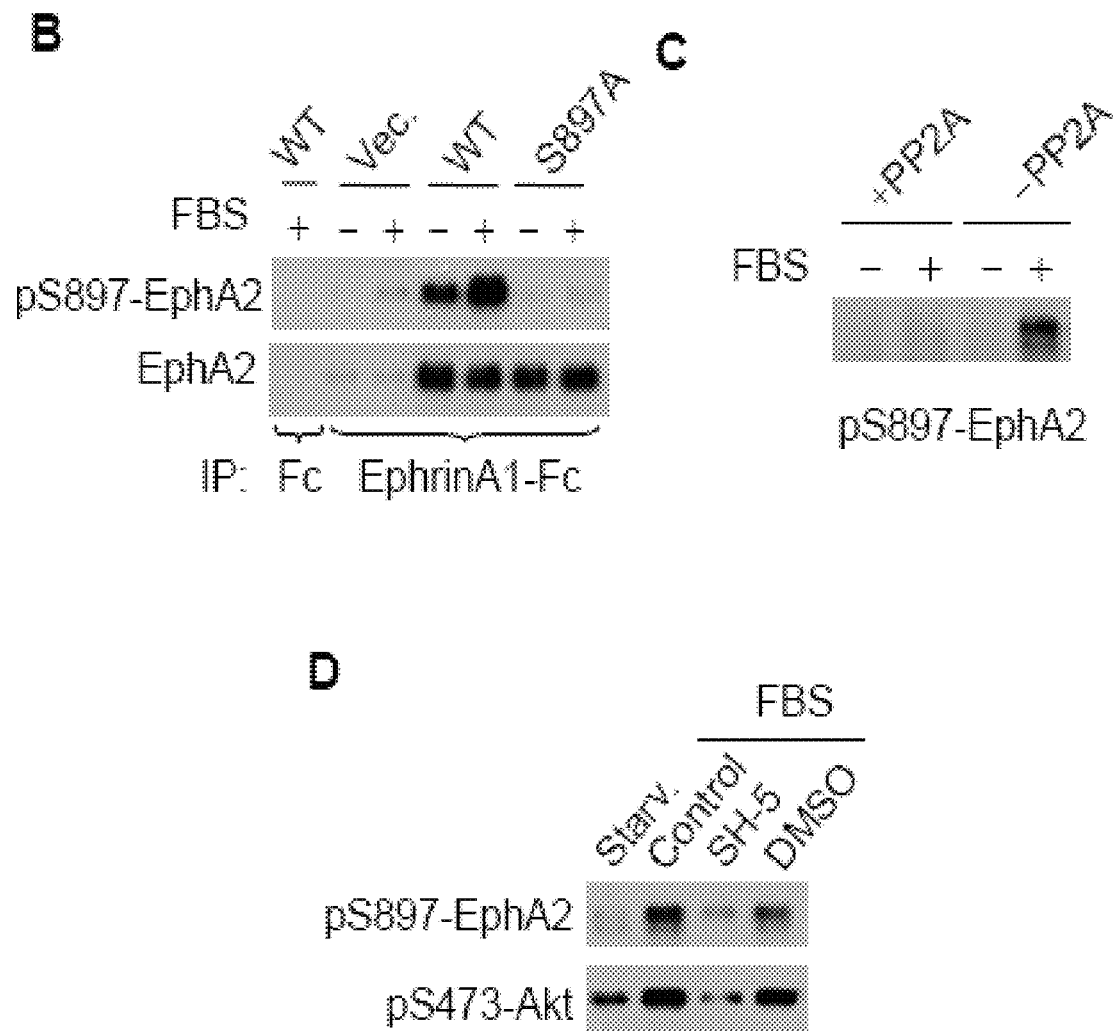
Fig. 5B-D

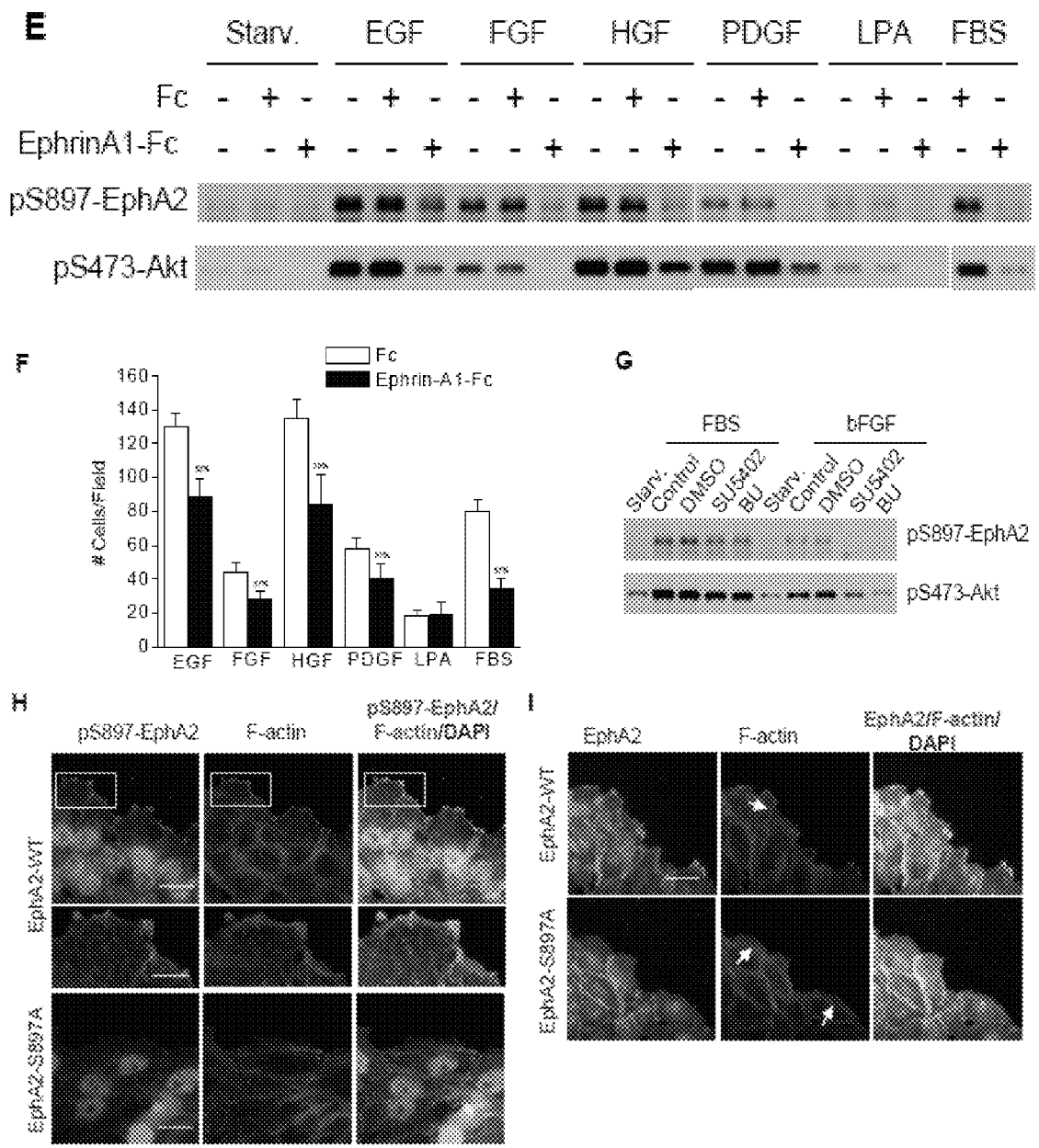
Fig. 5E-I

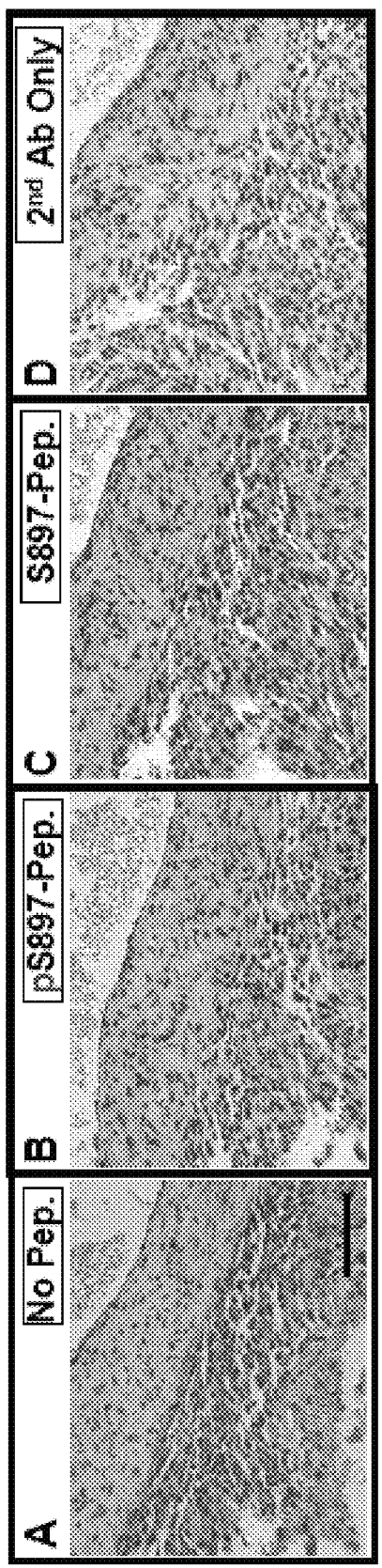
Fig. 6A-D

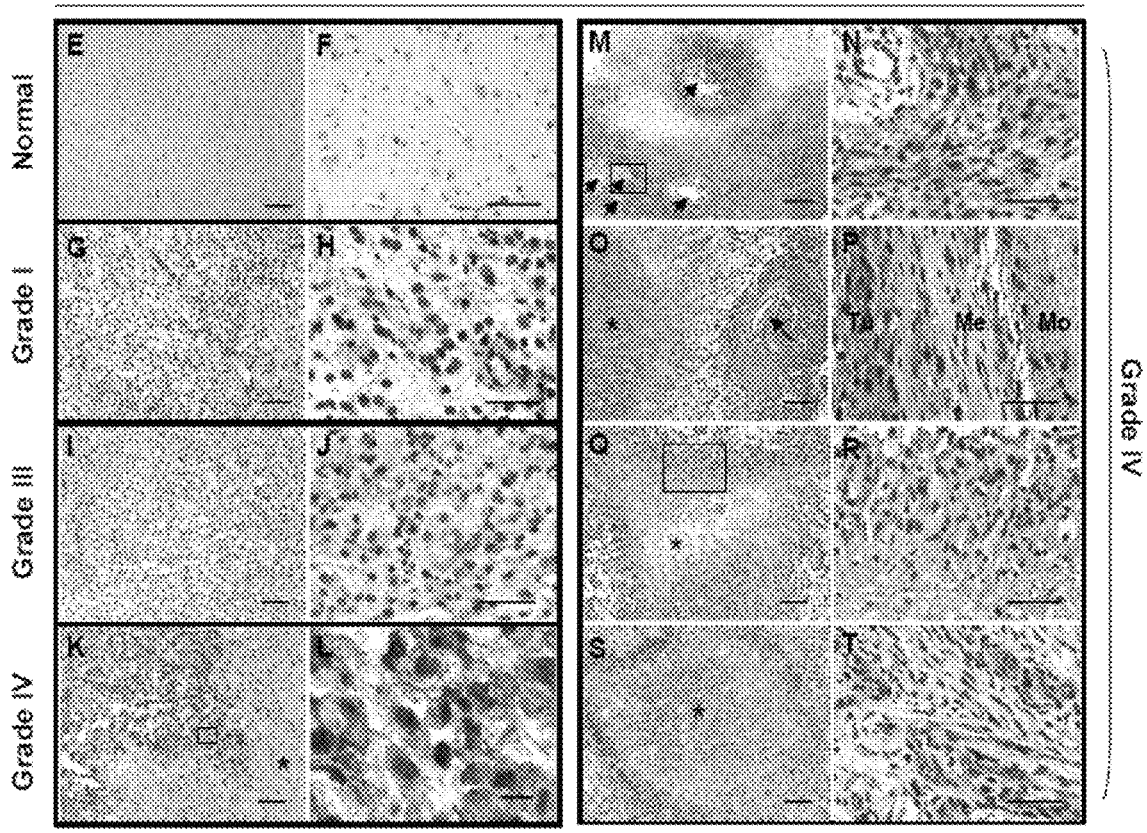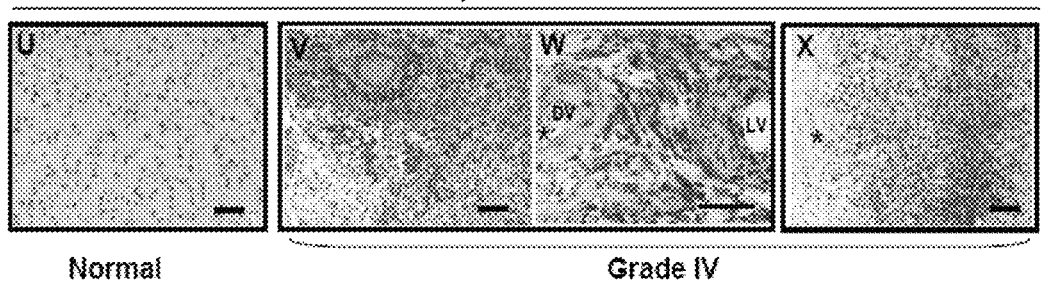
Fig. 6E-X

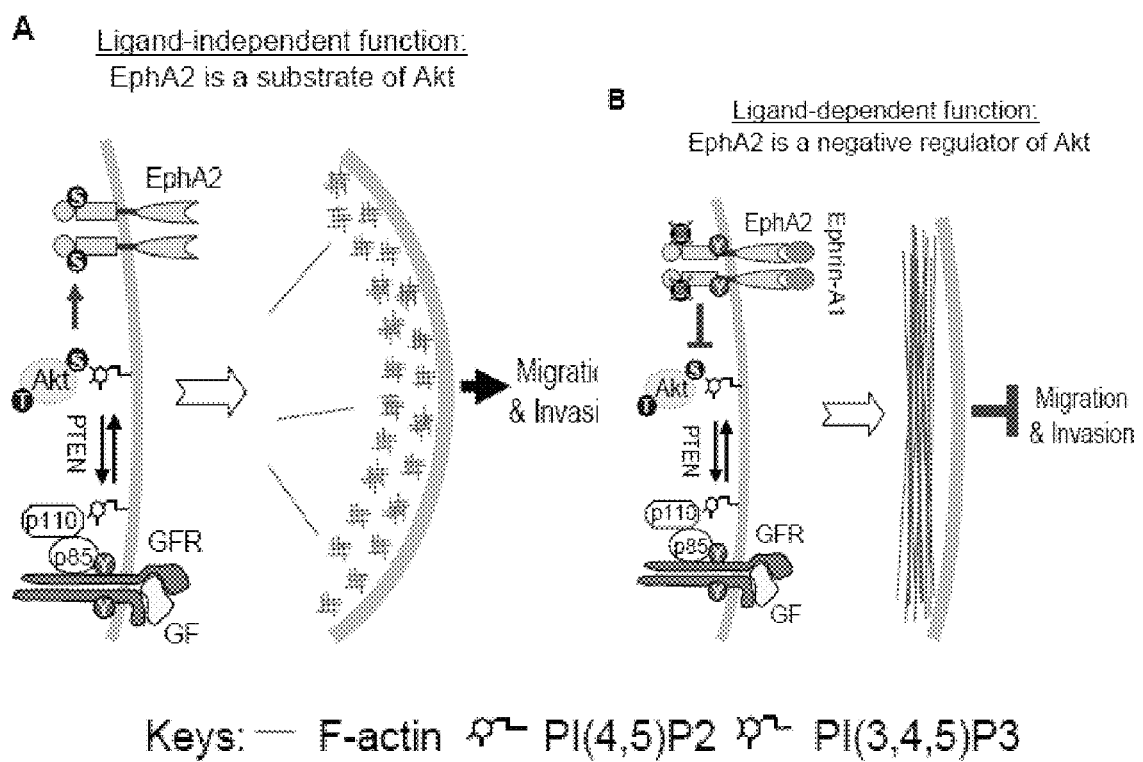
Fig. 7A-B

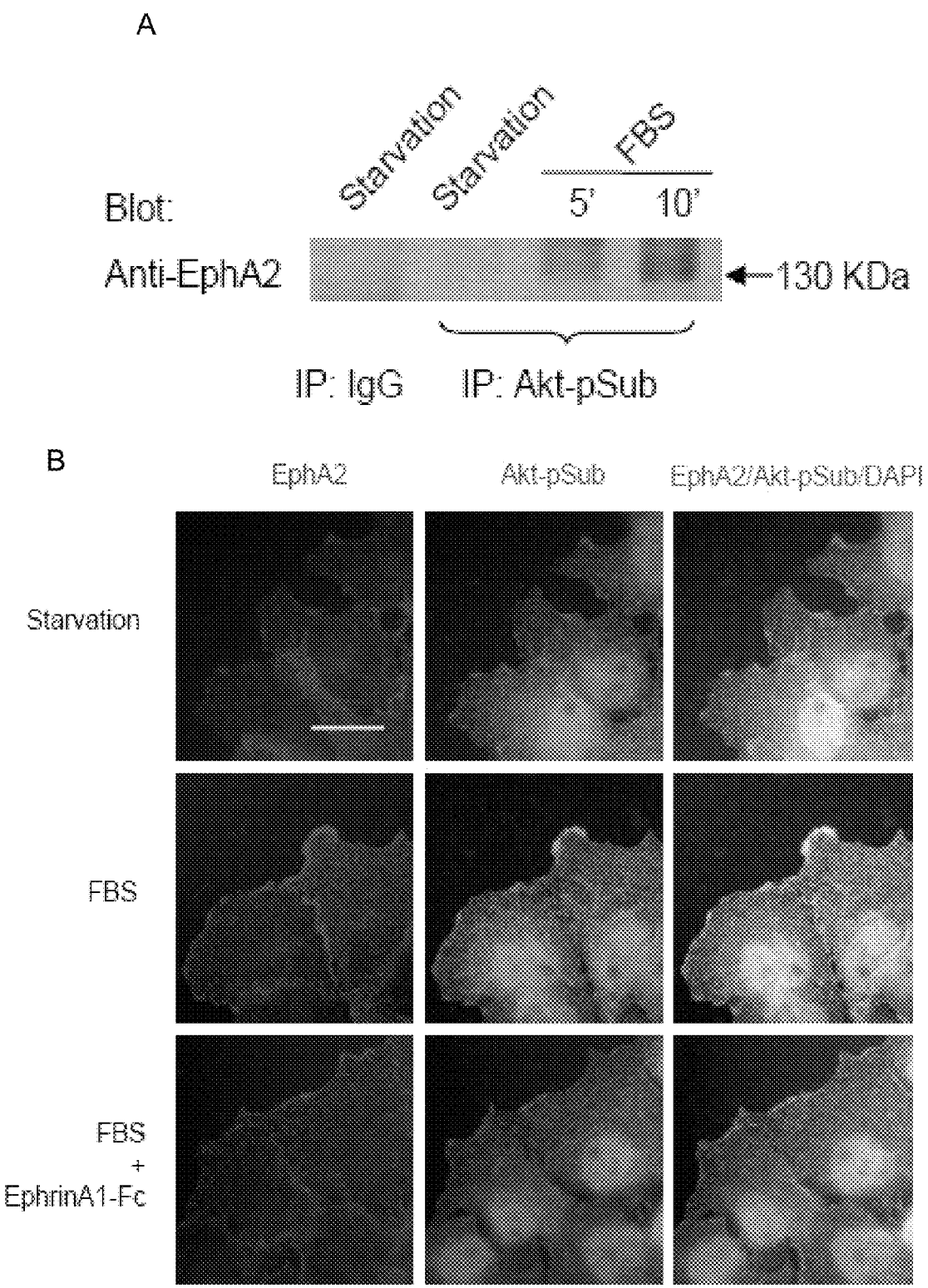
Fig. 8A-B

A
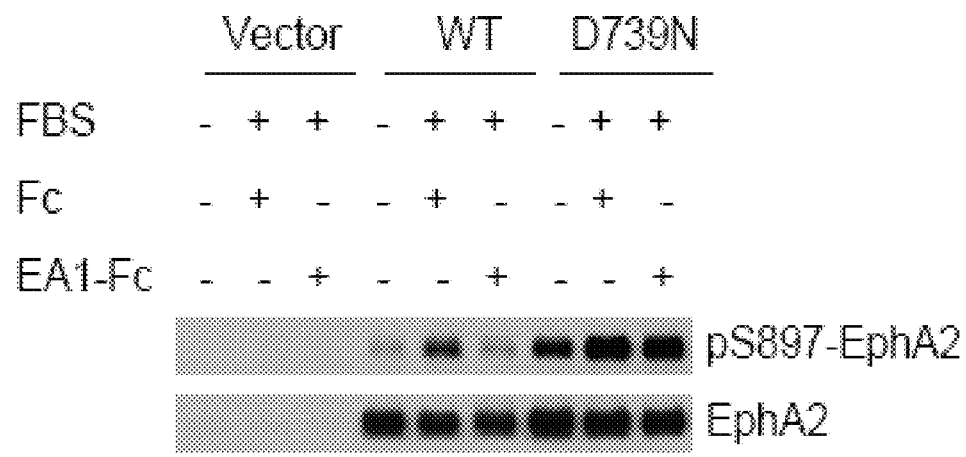
B
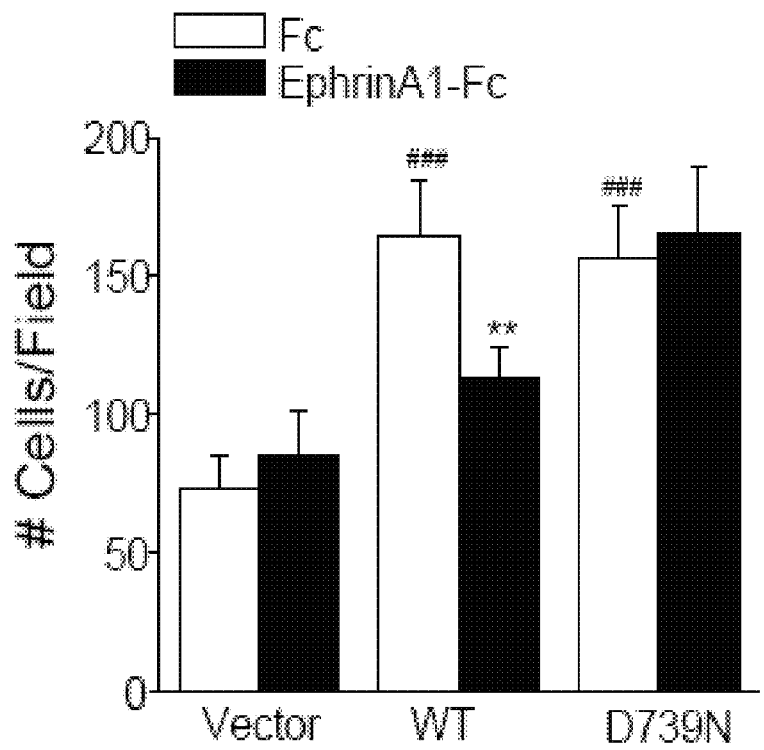
Fig. 9A-B

A
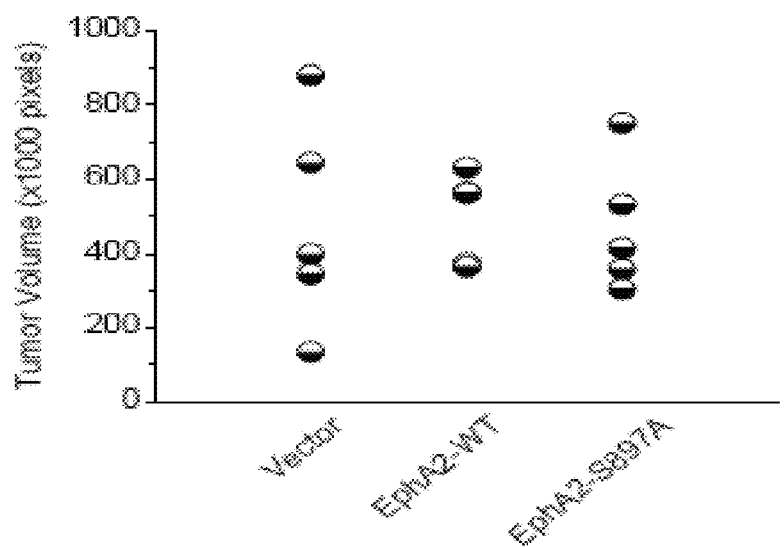
B
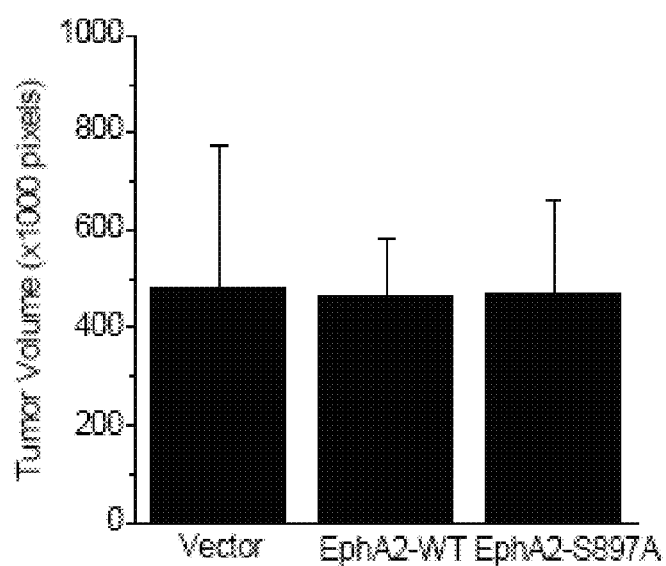
Fig. 15A-B

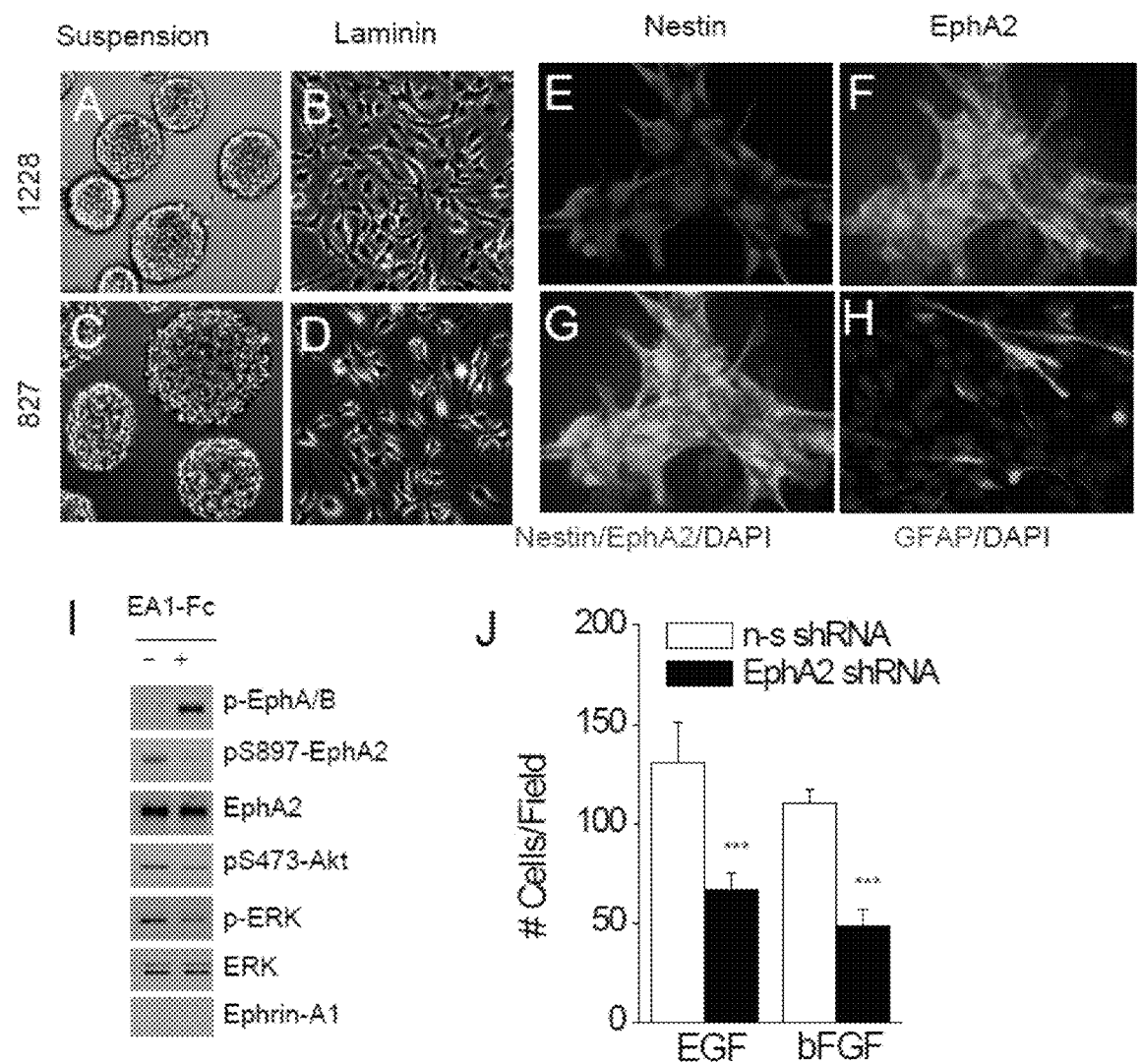
Fig. 16A-J

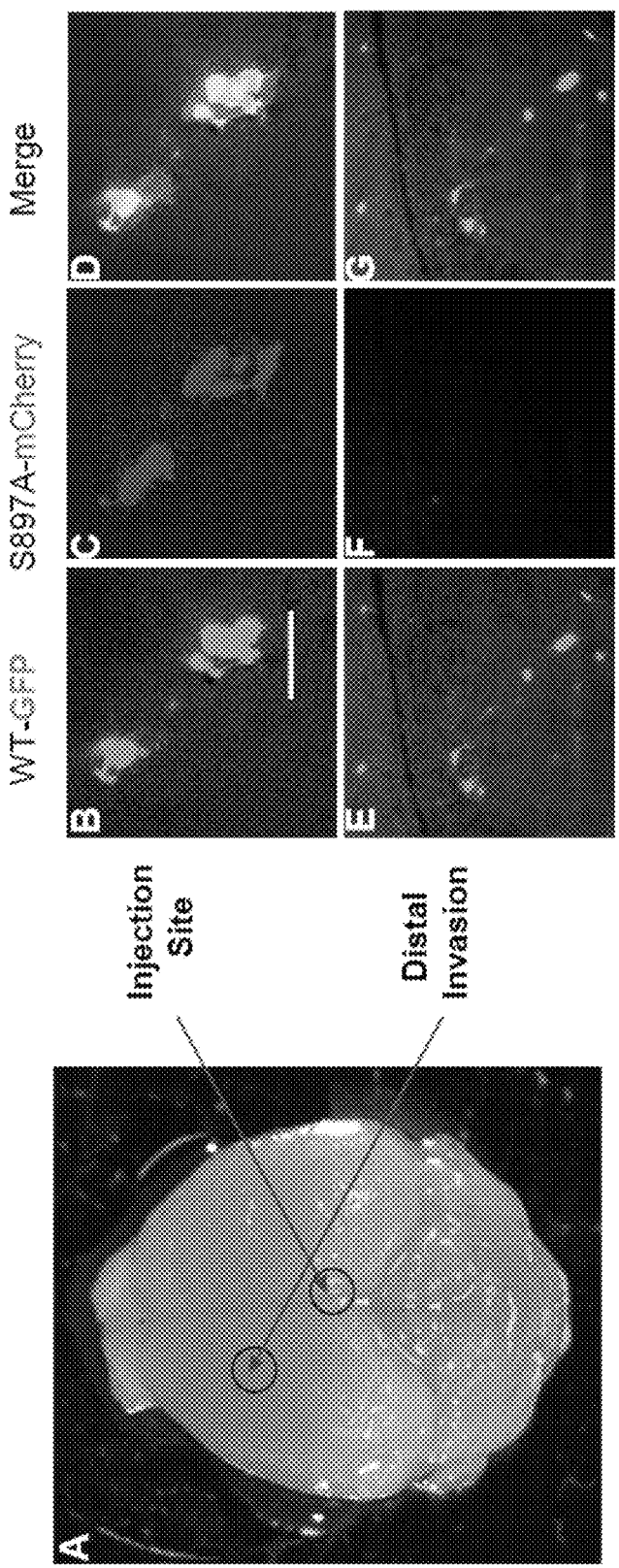
Fig. 18A-G

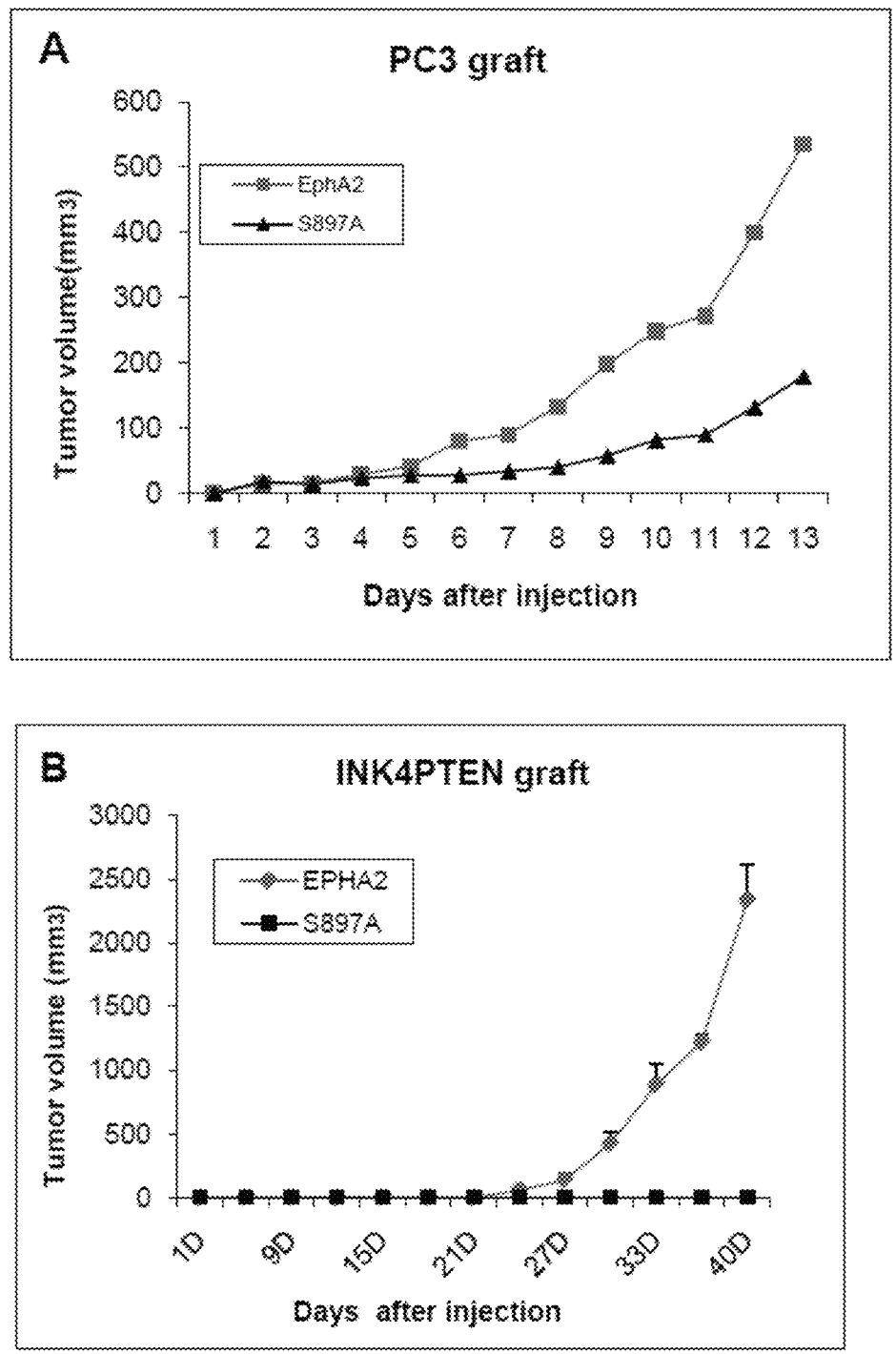
Fig. 19A-B

```
SEQUENCE LISTING

<160> NUMBER OF SEQ ID NOS: 1

<210> SEQ ID NO 1
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 1

Asp Pro Arg Val Ser Ile Arg Leu Pro Ser Thr Ser Gly Ser Glu Gly
1               5                   10                  15

Val Pro Phe Arg
            20
```

EPHA KINASE CANCER DIAGNOSTIC

RELATED APPLICATION

This application claims priority from U.S. Provisional Application No. 61/184,433, filed Jun. 5, 2009, the subject matter which is incorporated herein by reference.

GOVERNMENT FUNDING

This invention was made with government support under Grant No. NIH CA92259 and NIH R01 CA96533 awarded by The National Institute of Health. The United States government has certain rights in the invention.

BACKGROUND

Chemotactic cell migration plays an important role in tumor invasion by directing the spread of tumor cells towards growth factors. Tumor cells can move while attached to each other, which often occurs at early stage of cancer progression. During malignant progression, tumor cells can undergo epithelial to mesenchymal transition and adopt fibroblast-like cell migration or amoeboid movement, by which they migrate as individual cells. Although distinct in many aspects, different migration modes share similar signaling mechanisms. Phosphoinositide 3-kinases (PI3Ks) and Rho family of GTPases have been identified as key molecules in regulating cell migration. By generating PI(3,4,5)P3 at the proximity of chemoattractant, PI3Ks activity defines the leading edge of the migrating cell.

As a primary target of PI3Ks, Akt has well-documented roles in promoting cell survival, proliferation, and growth. Recent cancer genome analyses revealed Akt activation in vast majority of glioblastoma multiforme (GBM) through inactivation of Phosphatase/Tensin homolog deleted on chromosome 10 (PTEN), activation of receptor tyrosine kinases (RTKs) or amplification of Akt. PTEN loss and Akt activation also frequently occur in human prostate cancer. Increasing evidence show that Akt signaling regulates migration of many types of cells. As a key molecule situated at the nodal point where many signaling pathways converge, Akt has been proposed to modulate cell migration through several mechanisms. For instance, Akt activation leads to Rac activation and facilitates cell migration. Consistent with this notion, Akt promotes lamellipodia formation and growth factors induced cell migration by phosphorylating an actin crosslinking protein, Girdin, at cell leading edge. Activation of integrin-mediated cell adhesion at the leading edge of migrating cells is critical of productive cell motility. Akt activity is found to be necessary for both activation and recycling of several integrins. Cell migration is intrinsically linked to tumor invasion and metastasis. In prostate cancer and secondary glioma, accelerated loss of PTEN occurs late during tumor development and is linked to malignant progression.

The 16 members of vertebrate Eph constitute the largest subfamily of RTKs. Interaction of Eph receptors and their membrane-bound ephrin ligands leads to contact dependent bidirectional signaling into the opposing cells, which regulates diverse array of developmental and physiological processes. In addition, perturbation of Eph/ephrin systems has been documented in different types of human cancer. However, the exact role of Eph kinase in tumor etiology and progression has remained controversial. The case in point is EphA2 kinase that is among the most frequently affected Eph kinases in human cancer. It is overexpressed in a variety of human malignancies, and is associated with poor prognosis in several different tumor types including glioblastoma multiforme (GBM) and cancers of prostate, kidney, and lung. In several studies, overexpression of EphA2 has been linked to malignant progression. Paradoxically, activation of EphA2 kinase on tumor cells can trigger signaling events that are more consistent with a tumor suppressor. Thus, ligand stimulation of EphA2 inhibits integrin signaling, Ras/ERK pathway and Rac GTPases, which is correlated with inhibition of cell proliferation and migration. Furthermore, EphA2 is found to be a target gene for p53 family of proteins and causes apoptosis when over expressed. Further supporting tumor suppressor role of EphA2, we recently report dramatically increased susceptibility to skin carcinogenesis in EphA2 KO mice. The seemingly conflicting role of EphA2 kinase in the literature, either as an oncoprotein or a tumor suppressor, is an outstanding dilemma in cancer research today.

SUMMARY

The present invention relates generally to a method of detecting, characterizing, and/or determining migration, invasion, spreading, and/or progression of tumors in a subject. It was found that EphA2 is a novel substrate for the protein kinase Akt and that Akt-mediated phosphorylation at serine 897 in neoplastic cells (e.g., tumor and/or cancer cells) expressing EphA2 is the major mechanism responsible for EphA2 ligand-independent stimulation of neoplastic cell migration, invasion, spreading, and/or progression.

An aspect of the invention relates to a method of detecting malignant progression of neoplastic cells in an animal. The method includes the steps of: (1) obtaining a tumor sample from the animal; (2) determining a level of S897-EphA2 phosphorylation in the neoplastic cells of the sample; and (3) comparing the determined level of S897-EphA2 phosphorylation in the sample to a control value. An increased level of S897-EphA2 phosphorylation compared to the control value is indicative of malignant progression of the neoplastic cells in the animal.

Another aspect of the invention relates to a method of characterizing malignant progression of cancer cells in a mammal. The method includes the steps of: (1) obtaining a tumor sample from the animal; (2) determining a level of S897-EphA2 phosphorylation in the sample; and (3) comparing the determined level of S897-EphA2 phosphorylation in the sample to a control value. The greater the determined level of S897-EphA2 phosphorylation compared to the control value the greater the degree of tumor cell malignant progression in the mammal.

Another aspect of the present invention is directed to a method of determining the efficacy of a cancer therapeutic in inhibiting cancer cell migration, invasion, spreading, progression, and/or metastases. The method includes: (1) administering a therapeutic agent to the animal; (2) obtaining a tumor sample from the animal; (3) detecting a level of pS897-EphA2 in the sample; and (4) comparing the detected level of pS897-EphA2 in the sample to a control. A reduced level of pS897-EphA2 in the sample compared to the level of pS897-EphA2 in the control sample is indicative of an effective cancer therapeutic or an effective combination of cancer therapeutics in inhibiting cancer cell migration, invasion, spreading, and/or progression.

A further aspect of the present invention relates a method of screening agents that affect at least one component of the receptor RTK/PI3K/PTEN/AKT/mTOR pathway in a cell. The method includes: (1) administering an agent to a cell expressing EphA2; (2) detecting the level of pS897-EphA2 in the cell; and (3) comparing the detected level of pS897-

EphA2 in the cell to a control. An increased level of pS897-EphA2 in the cell or a decreased level of pS897-EphA2 in the cell compared to the control is indicative of an effective agent.

Yet another aspect of the present invention relates to a method of measuring Akt phosphorylation in a cell. The method includes administering an anti-pS897 antibody or fragment thereof to the cell; (2) measuring the level of bound antibody or fragment thereof in the cell; and (3) comparing the level of the bound antibody to a control value. An increase in the amount of bound antibody compared to the control value is indicativ of an increased amount of Akt phosphorylation in the cell. A decrease in the amount of bound antibody compared to the control value is indicativ of a decreased amount of Akt phosphorylation in the cell.

Another aspect of the invention relates to a method of inhibiting neoplastic cell migration and invasion is provided. The method includes administering to a neoplastic cell expressing EphA2 a therapeutically effective amount of an agent that targets S897-EphA2 and inhibits phosphorylation of S897 of EphA2. In aspect of the invention, the agent can include antibody and/or fragment thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Figure 1K:
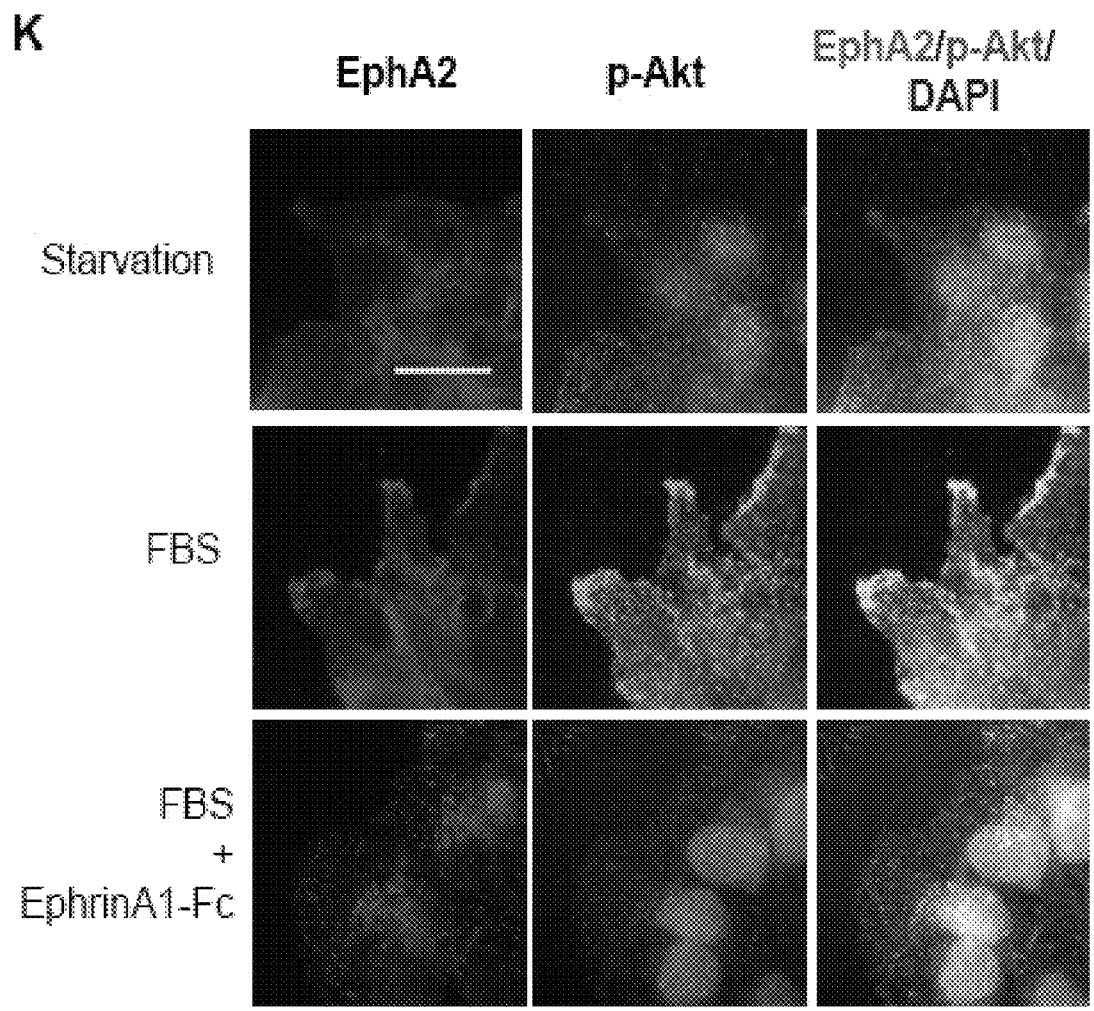
FIG. 1 illustrates EphA2 possesses both ligand-independent and ligand-dependent functions in regulating growth factor-induced chemotactic cell migration and signaling. A-B. Ectopic overexpression of EphA2 enhances serum-induced chemotactic cell migration in a ligand-independent manner. U373 cells were infected with retroviral vector expressing EphA2. Cells were stimulated with ephrinA1-Fc, and lysates were blotted for active (p-EphA/B) or total EphA2 (A). The infected cells were subjected to Boyden chamber cell migration assay (B) with 5% FBS in lower chamber as chemoattractant. Cell numbers from 6 randomly selected fields were counted. Numbers represent mean±S.D.*, p<0.001; ###, p<0.001. C-F. Downregulation of EphA2 by shRNA reduces serum-stimulated chemotaxis of U373 and PC-3 cells. EphA2 shRNA or control GFP shRNA was introduced into U373 (C-D) and PC-3 cells (E-F) via Lentiviral infection. Stable cell lines were subjected to immunoblot (C, E) or chemotactic cell migration assay (D, F) as described for B. Numbers represent mean±S.D., p<0.01;***, p<0.001; ##, p<0.01; ###, p<0.001. G-H. Serum stimulation results in S/T phosphorylation of EphA2 downstream from Akt activation, which is inhibited by ephrinA1 co-stimulation. Serum-starved cells were scratch-wounded and stimulated with FBS for the indicated times in absence and presence of ephrinA1-Fc. Total cell lysates (G) or EphA kinase precipitates (H) were subjected to immunoblot with the indicated antibodies. I. Serum stimulation-induced EphA2 phosphorylation at Akt substrate sites is abolished by pretreating cells with LY294002. Experiments were performed as described in G-H except that 10 μM of LY294002 was added to the cells 1 hour prior serum-stimulation. J. Serum stimulation-induced EphA2 phosphorylation at Akt substrate sites is inhibited by DN-Akt. U373 cells that stably expressed DN-Akt or control vector were stimulated and analyzed as described in G-H. K.

EphA2 kinase activation by ephrinA1 inhibits leading edge localization of phosphorylated Akt. Cells were starved and wounded as described above. After stimulation for 10 min with FBS in the absence and presence of ephrinA1-Fc, cells were fixed and stained with mouse anti-EphA2 and rabbit anti-pS473-Akt, followed by detection with fluorescence-conjugated secondary antibodies. Scale bar, 25 μm.

FIG. 2 illustrates Serine 897 of EphA2 is the major substrate site for activated Akt, which is essential for ligand-independent promotion of cell migration. A. Schematic illustration of relative positions of putative Akt substrate sites in EphA2 cytoplasmic tail. B. S897A mutation abolishes serum-induced S/T phosphorylation of EphA2. HEK 293 cells were infected with retroviral vectors expressing wild type or mutant EphA2. EphA kinases were precipitated with ephrinA1-Fc and immunoblotted for Akt-pSub and total EphA2. C. Immunofluorescence staining of infected HEK 293 cells shows that the exogenous EphA2 receptors were homogeneously expressed. Scale bar, 25 μm. D. Both S897A and S897D mutation completely abolishes the serum-induced phosphorylation of EphA2 on Akt substrate sites. Cells were stimulated and analyzed as described in B. E. Overexpression of WT-EphA2 but not S897A-EphA2 or S897D-EphA2 enhances serum-stimulated cell migration. Boyden chamber cell migration assay was performed as described in FIG. 1. Cell numbers from 6 randomly selected fields were counted. Numbers represent mean±S.D.***, p<0.001.

FIG. 3 illustrates the overexpression of wild type EphA2 promotes serum-induced chemotactic migration of U87 and U373 glioma cells as well as PC-3M prostate cancer cells, and the effects were abolished by expression of S897A-EphA2 mutant. A-B. Overexpression of WT-EphA2 and S897A-EphA2 in U87, U373, PC-3M, A172, T98G, and LN229 cells by retroviral infection. C-D. Chemotaxis towards serum was promoted by overexpression of WT-EphA2 but not S897A-EphA2. Boyden chamber cell migration assay was performed as described in FIG. 1. Numbers represent mean±S.D.*, p<0.05;, p<0.01;*, p<0.001. E-H. Restoration of PTEN expression in PTEN-null U373 cells dramatically inhibited basal cell migration. (E) PTEN re-expression significantly reduced FBS-induced Akt activities, which was quantified in FIG. 4F. In both Boyden chamber migration (G) and scratch wound (H) assays, PTEN restoration reduced cell migration.

FIG. 4 illustrates EphA2 ligand-dependent inhibition of cell migration and invasion are not affected by S897A mutation. A-F. S897A mutation of EphA2 does not affect its ligand-dependent inhibitory effect on migration (A-C) and invasion (D-F) of U373, U87, and A172 cells expressing WT-EphA2, S897A-EphA2, or control vector. In both assays, 5% FBS was used as chemoattractants. Numbers represent mean±S.D. from 6 randomly selected fields.*, p<0.05; , p<0.01; *, p<0.001 compared to Fc control of the same cell line. ##, p<0.01; ###, p<0.001 compared to Fc control of vector cells. G. Overexpression of WT-EphA2 induces a polarized morphology and enhanced chemokinetic motility, which is inhibited by S897A mutation. Cells were plated at low density in 6-well dishes, and subject to time-lapse analysis to monitor chemokinetic migration. The stills at 0 and 360 min are shown. Asterisks indicate cells that have gained net translocation.

FIG. 5 illustrates multiple growth factors can induce S897 phosphorylation of EphA2, which is required for EphA2 localization to the leading edge and for cell polarization. A-B. Characterization of a rabbit polyclonal antibody against S897 phospho-peptide. Serum-starved 293 HEK cells that express vector, WT-EphA2, or S897A-EphA2 were stimulated with 10% FBS in the absence and presence of ephrinA1-Fc for 10 min. Total cell lysates (A) and EphA kinase precipitates (B) were analyzed by immunoblotting with polyclonal anti-pS897-EphA2 and total EphA2. C. PP2A treatment causes dephosphorylation of serum-induced pS897-EphA2. Serum-stimulated U373 cells were subjected to PP2A phosphatase assay as described in Methods. Cell lysates were blotted with polyclonal anti-pS897-EphA2. D. Inhibition of Akt by Akt inhibitor II (SH-5) abolishes serum-induced pS897-EphA2. Serum-starved U373 cells were pretreated with 10 μM SH-5 for 30 min and then stimulated with FBS for 10 min. Cell lysates were analyzed by immunoblotting with polyclonal anti-pS897-EphA2 and pS473-Akt. E-F. Growth factors induce S897 phosphorylation of EphA2 (E) and migration (F) in U373 cells, which is inhibited by co-stimulation with ephrinA1. E. Serum-starved U373 cells were stimulated with 10 ng/ml of EGF, bFGF, PDGF, HGF, 10% FBS, or 10 μM LPA alone or in combination with 1 μg/ml Fc or ephrinA1-Fc for 10 min. Total cell lysates were analyzed by immunoblotting with rabbit polyclonal anti-pS897-EphA2 and anti-pS473-Akt. F. U373 cell migration toward same concentrations of growth factors and LPA or 5% FBS. The numbers over solid bars show the percentage of inhibition by ephrin-A1. G. Inhibition of FGFR is not sufficient for inhibiting serum-induced pS897-EphA2. Serum-starved U373 cells were pretreated with 10 μM SU5402 or 100 nM 1-(2-Amino-6-(3,5-dimethoxyphenyl)pyrido[2,3-d]pyrimidin-7-yl)-3-tert-butyl urea (BU) for 30 min. Cells were then stimulated with 10% FBS for 10 min. Cell lysates were analyzed by immunoblotting with polyclonal anti-pS897-EphA2 and pS473-Akt. H. Phospho-S897-EphA2 is localized to the leading edge and the tips of actin stress fibers. Serum-starved cells were treated and processed for IF staining as in FIG. 1K. Scale bar, 25 μm in top and bottom row, 10 μm in the zoomed images. I. Cells expressing S897A-EphA2 show defective cell polarization, which was correlated with mislocalization of the mutant proteins to cell-cell junctions. Scale bar, 25 μm.

FIG. 6 illustrates the levels of S897 phosphorylation of EphA2 in human glioma specimens are correlated with tumor grades and overlap with active Akt. Paraffin sections of normal human brain and astrocytomas were stained immunohistochemically using rabbit polyclonal anti-pS897-EphA2 and anti-pS473-Akt. A-D. Rabbit polyclonal anti-pS897-EphA2 specifically recognizes pS897-EphA2 in paraffin sections. Paraffin sections of human astrocytomas were stained immunohistochemically with untreated antibody (A) or antibody preincubated with phospho-S897 peptide (B) or unphosphorylated S897 peptide (C). The sections processed with omission of primary antibody were served as the negative control (D). Scale bar, 50 μm. E-F. Normal brains were negative for pS897-EphA2. Scale bar, 200 μm in E, 100 μm in F. G-J. Grade I (G, H) and grade III (I, J) astrocytomas showed low immunoreactivities for pS897-EphA2. Scale bar, 100 μm in G and I, 50 μm in H and J. K-T. Grade IV astrocytomas or GBM, showed high levels of pS897-EphA2. Positive tumor cells next to a necrotic area indicated by an asterisk (K, scale bar, 100 μm). High power inset (L, scale bar, 10 μm) shows the membrane expression pattern of pS897-EphA2 by tumor cells. M-N. Perivascular staining pattern of pS897-EphA2. N, inset from M. scale bar, 200 μm in M, 50 μm in N. Blood vessels are indicated by arrows. O. Phospho-S897-EphA2 was abundantly detected at the interface between necrosis (asterisk) and vasculature (arrow). Scale bar, 100 μm. P. Phospho-S897-EphA2 was present at high levels in the meningeal invasion. Positive tumor cells (Tu) invaded meninges (Me) and were further infiltrating the molecular layer of adjacent side of the gyro (Mo). Scale bar, 50 μm. Q-S. Phospho-S897-EphA2 was detected in the pseudopalisading cells surrounding necrotic foci (Asterisk indicates necrosis). R, High power inset from Q. Scale bar, 100 μm in Q and S, 50 μm in R. T. S897 phosphorylation of EphA2 was also abundant in microvasculature proliferation, another distinguishing feature of GBM. Scale bar, 50 μm. U-X. Phospho-S473-Akt expression in GBM. pS473-Akt was most abundant in tumor cells surrounding blood vessels (V, W) or necrotic regions (X) where pS897-EphA2 presented at high levels. DV, dead vessel. LV, live vessel. Asterisk indicates necrosis. Scale bar, 100 μm in U, V and X; 50 μm in W.

FIG. 7 illustrates a model depicting ligand-dependent inhibition and ligand-independent stimulation of cell migration by EphA2. A. In the absence of ligand, EphA2 is a substrate of Akt activated in tumor cells due to growth factor receptor activation or loss of PTEN. EphA2 phosphorylated on S897 promotes cell polarization, lamellipodium protrusion and cell migration. S897A mutant EphA2 is sufficient to block chemotactic cell migration. B. EphrinA1 stimulation causes tyrosine phosphorylation in the juxtamembrane domain and serine dephosphorylation on S897 of EphA2, which prevents lamellipodium protrusion and inhibits cell migration.

FIG. 8A illustrates the detection of EphA2 in Akt phospho-substrates immunoprecipitates. Cell lysates subjected to immunoprecipitation with anti-Akt-pSub antibodies. The precipitated materials were probed with an antibody against EphA2. B. EphA2 colocalizes with Akt phospho-substrates at migrating cell leading edge upon serum stimulation, which is inhibited upon EphA2 kinase activation by ephrinA1 stimulation. U373 cells were starved, wounded as described above. After stimulation for 5 min with FBS in the absence and presence of ephrinA1, cells were fixed and stained with mouse polyclonal anti-EphA2 and rabbit polyclonal anti-Akt-pSub, followed by detection with fluorescence conjugated secondary antibodies. Scale bar, 25 μm.

FIG. 9 illustrates EphA2 kinase activity is not required for phosphorylation of S897-EphA2 and promotion of migration by EphA2 overexpression. WT- or D739N-EphA2 were introduced into HEK 293 via retroviral infection. A. Stable cell lines were plated and starved in 1% FBS. Staved cells were stimulated with 10% FBS in the presence of 1 μg/ml of Fc or ephrin-A1-Fc for 10 min. Cell lysates were probed for pS897-EphA2 and EphA2. B. Cells were subjected to Boyden chamber migration assay. Numbers represent mean±S.D. from 6 randomly fields. **, p<0.01 compared to Fc control of the same cell line. ###, p<0.001 compared to Fc control of vector cells.

Figure 10:
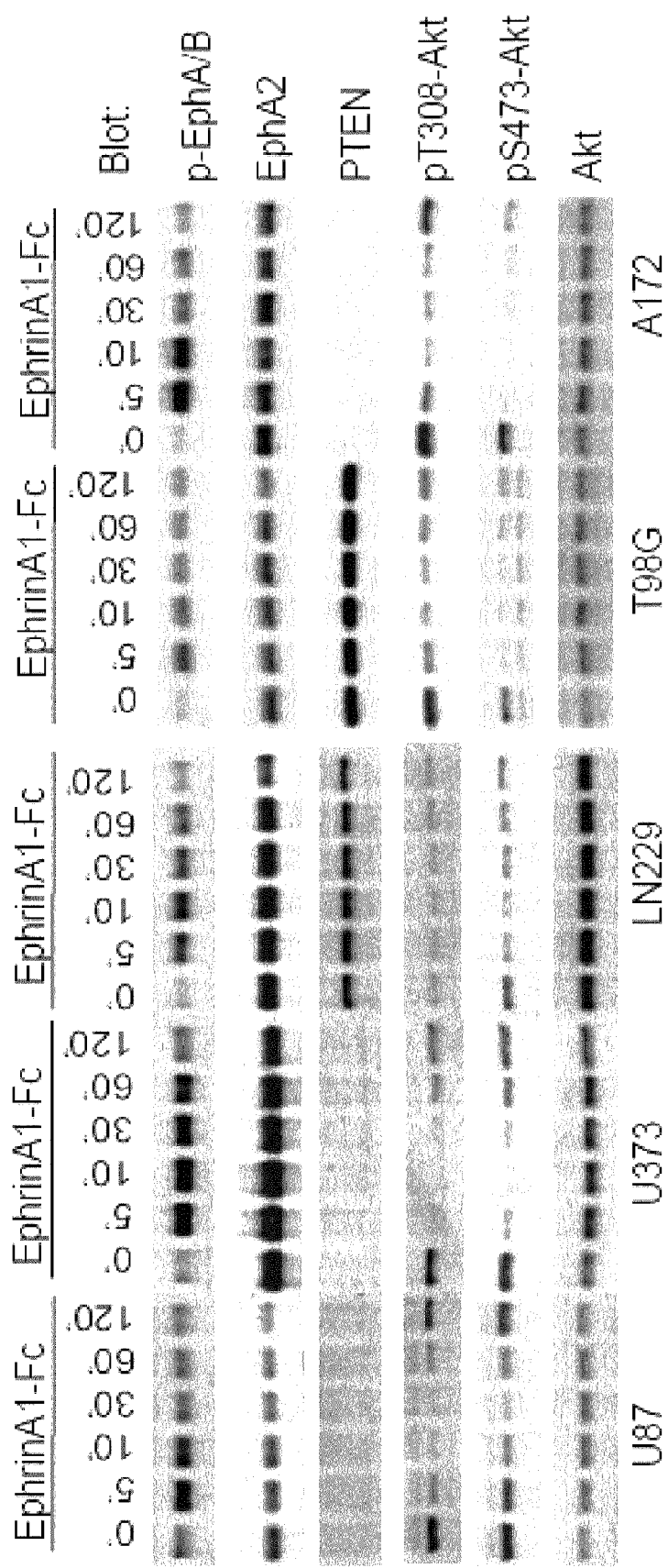

FIG. 10 illustrates EphrinA1 stimulation of EphA2 preferentially inhibits Akt activation in PTEN-deficient glioma cells. Subconfluent cells were stimulated with ephrinA1-Fc for the indicated times and lysed. Total cell lysates were analyzed by immunoblotting with the antibodies as indicated.

Figure 11:
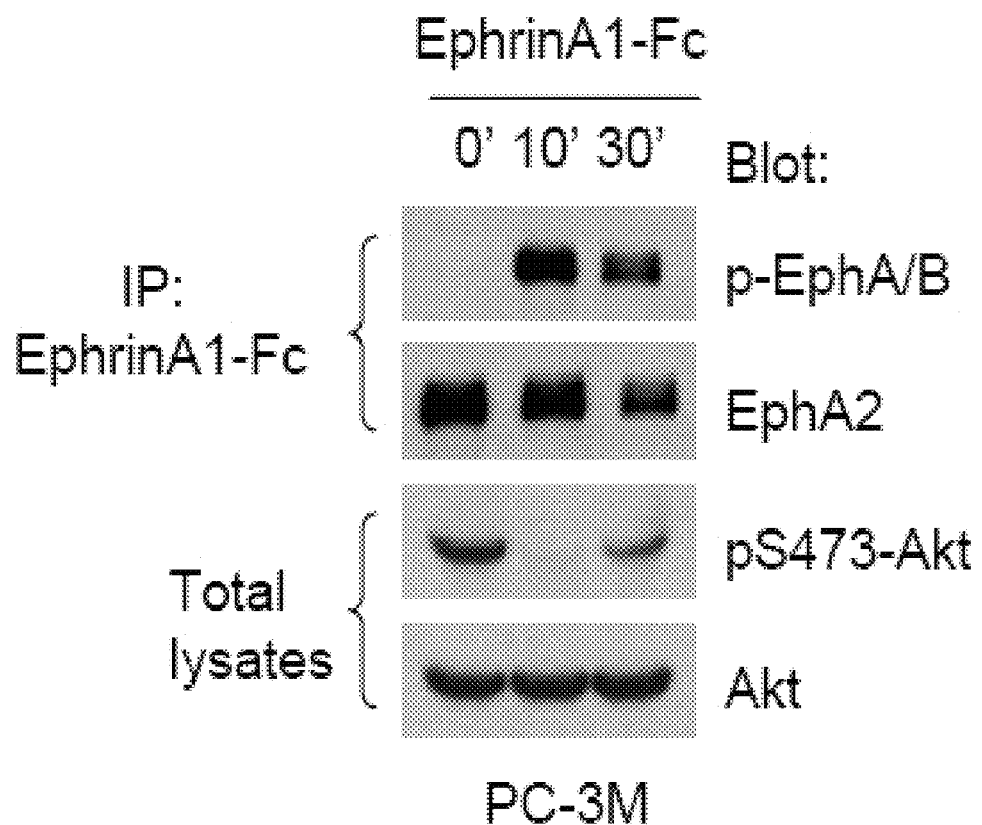

FIG. 11 illustrates EphA2 kinase activation by ephrin-A 1 stimulation inhibits Akt activation in migrating PC-3M cells. Confluent cells were scratch-wounded to induce cell migration. Four hours after wounding cells were stimulated with 1 μg/ml ephrinA1-Fc for the indicated times. Total cell lysates were subjected to immunoblot with the indicated antibodies.

Figure 12:
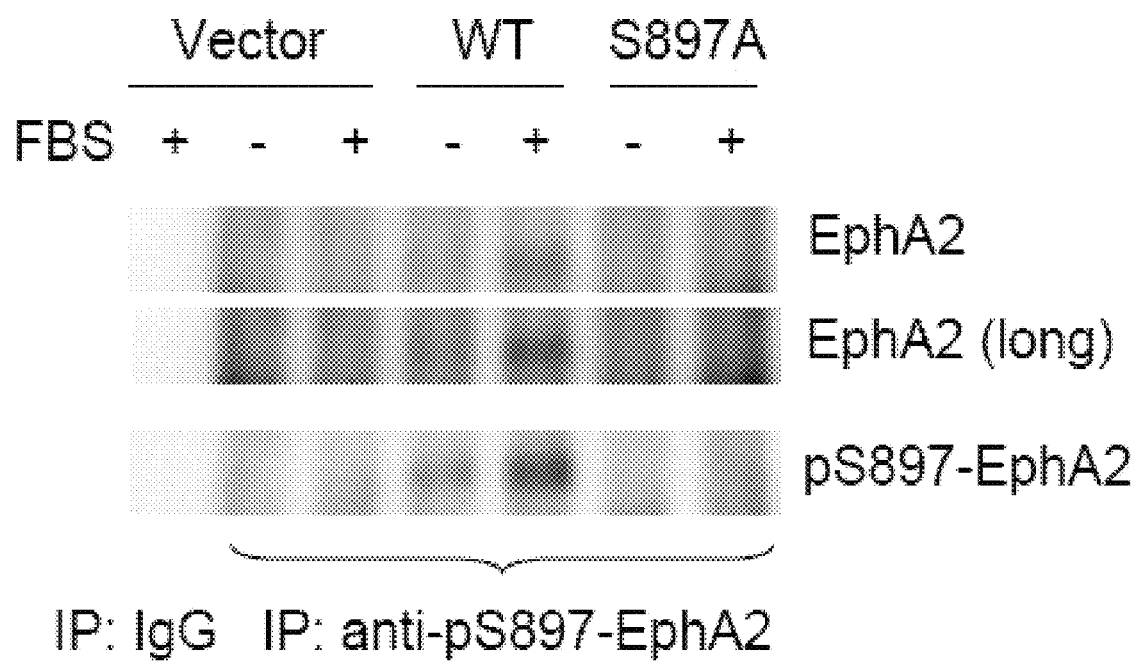

FIG. 12 illustrates the detection of EphA2 in pS897-EphA2 immunoprecipitates. Serum-starved 293 HEK cells that express vector, WT-EphA2, or S897A-EphA2 were stimulated with 10% FBS for 10 min. Total cell lysates were subjected to immunoprecipitation with rabbit polyclonal anti-pS897-EphA2. The precipitates were analyzed by immunoblotting with EphA2 and anti-pS897-EphA2.

Figure 13:
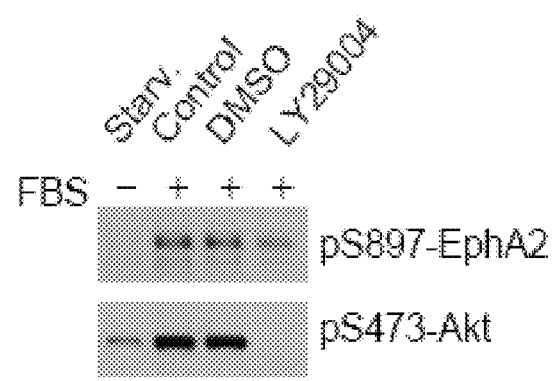

FIG. 13 illustrates the inhibition of PI3K abolishes serum-induced pS897-EphA2. Serum-starved U373 cells were pretreated with 10 μM LY294002 for 1 hour and then stimulated with FBS for 10 min. Cell lysates were analyzed by immunoblotting with polyclonal anti-pS897-EphA2 and pS473-Akt.

Figure 14:
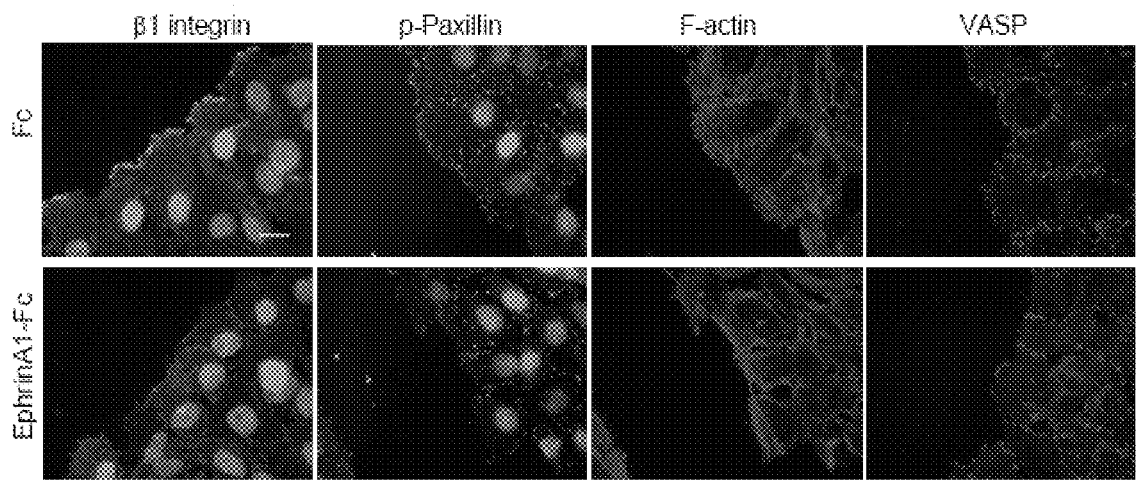

FIG. 14 illustrates EphrinA1 stimulation of glioma cell line U373 inhibits β1-integrin localization at leading edge and actin cytoskeltal structure during cell migration. Freshly confluent U373 cells were scratch-wounded to induced cell migration. Four hours after wounding, cells were stimulated with 1 µg/ml ephrinA1-Fc or Fc for 10 min. Cells were fixed and stained with rabbit polyclonal anti-β1-integrin and anti-p-paxillin, or mouse monoclonal anti-VASP. F-actin was stained with Texas Red-conjugated phalloidin. Scale bar, 25 µm.

FIG. 15 illustrates the overexpression of EphA2 does not affect intracranial growth of U87 tumors. U87 cells expressing vector, wild type or mutant EphA2 were implanted stereotactically into brains of nude mice. Brain sections were prepared 3 weeks post implantation and stained with rabbit anti-human vimentin. Tumor volumes were estimated from consecutive sections. A. Tumor volumes from each individual mouse. B. The average tumor volumes of each group of mice. Numbers represent mean±S.D, n=5.

FIG. 16 illustrates EphA2 is highly expressed on glioma stem cells (GSC) cells and is phosphorylated on S897. GSC 1228 and 827 cells were cultured in suspension (A,C) and on laminin (B,D). The 1228 line of GSC cells were plated on laminin and subjected to immunofluorescent analysis for Nestin (E) and EphA2 (F). Which were merged with DAPI in (G). (H) A fraction of 1228 GSC cells also express GFAP, a differentiation marker. (I) EphA2 in 1228 cells was phosphorylated on S897 in the absence of ligand stimulation. Ephrin-A1 treatment led to EphA2 activation, and inhibition of Akt and pS897-EphA2. (J) EphA2 shRNA knockdown inhibited chemotactic migration of GSC cells toward to EGF and bFGF. n-s shRNA: non-silencing shRNA.

Figure 17:
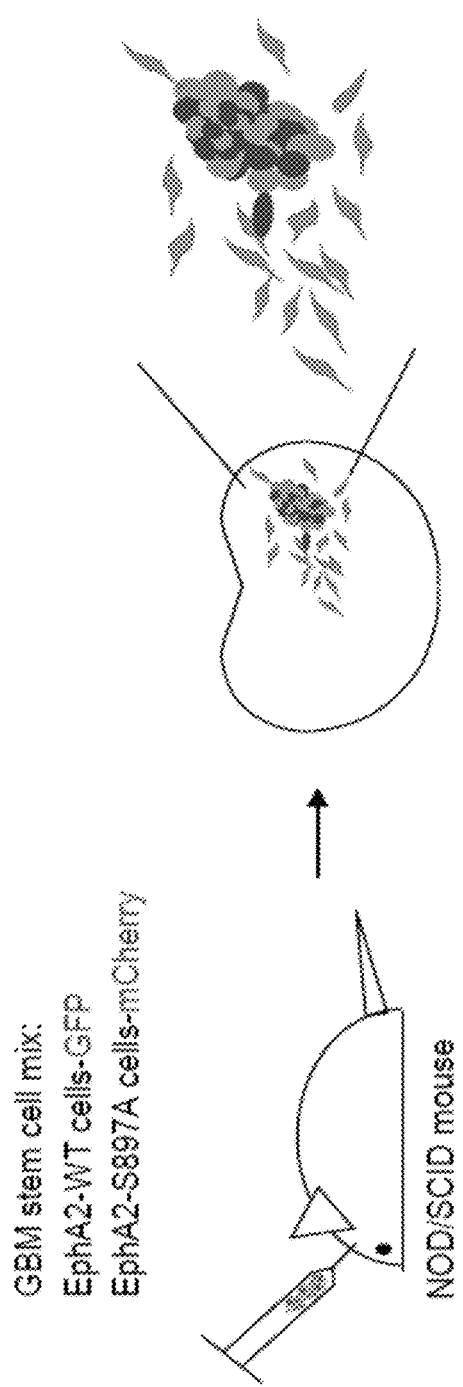

FIG. 17 illustrates pair-wise comparison strategy to evaluate the role of Akt-mediated phosphorylation of EphA2 on serine 897 (S897) on in vivo invasion of human GSC cells upon intracranial injection.

FIG. 18 (A-G) illustrates S897A mutation of EphA2 retarded diffuse invasion of glioma progenitor/stem cells (GSC) in NOD/SCID mouse brain suggesting an essential role of Akt-EphA2 crosstalk in glioma invasion in vivo.

FIG. 19 illustrates Akt-mediated phosphorylation of S897 of EphA2 is required for tumor xeno graft in viva A) PC3 human prostate cancer cells were stably infected with retroviral vectors expressing wild type or S897A mutant EphA2. The cells were then implanted subcutaneously into the hind flanks of 6 weeks old nude mice and tumor growth monitored by a digital caliper. B) A mouse glioma stem cell (GSC) line with Ink4 and PTEN double knockout were similarly infected with wild type or S897 mutant EphA2 and injected subcutaneously.

DETAILED DESCRIPTION

The present invention relates to diagnostic, prognostic, and therapeutic methods involving EphA2 phosphorylation and the RTK/PTEN/PI3K/Akt/mTOR pathways leading to cancer cell migration, invasion, spreading, and/or progression. The methods of the present invention generally involve detecting levels of EphA2 phosphorylation at serine 897 (S897) in neoplastic cells (e.g., cancer cells and/or tumor cells) or cell lysate and comparing the level to a control value.

EphA2 is a novel substrate for the protein kinase Akt. Akt is well known as a key signaling protein in cellular pathways leading to tissue growth, and aberrant Akt phosphorylation has been implicated as a major factor in many types of disorders, including cancer. Sequence analysis of EphA2 was used to identify potential serine/tyrosine sites (S/T sites) including S897, which resemble the consensus motif of known Akt substrates. Serine 897 is located in the linker region between the EphA2 kinase domain and sterile α motif (SAM), which is exposed and accessible to Akt phosphorylation and is the major site for Akt kinase phosphorylation in EphA2.

It was found that Akt-mediated S897 phosphorylation, in cells expressing EphA2, is the major mechanism responsible for ligand-independent stimulation of neoplastic cell (e.g., tumor cell or cancer cell) migration, invasion, spreading, and/or progression. Akt phosphorylated EphA2 is preferentially targeted to the migrating front of tumor cells, which is required to promote assembly of actin cytoskeleton and extension of lamellipoida. Promotion of chemotaxis by EphA2 in neoplastic cells, such as glioma and prostate cancer cells, requires S897 phosphorylation by Akt. Furthermore, the degree of S897-EphA2 phosphorylation was shown to be correlated with malignant tumor progression in human cancers. Thus, the degree and/or level of S897-EphA2 (pS897-EphA2) phosphorylation can be a marker for detecting and/or characterizing malignant progression of cancer cells.

A first aspect of the invention relates to a method of detecting malignant progression of neoplastic cells in an animal is provided. The method includes (1) obtaining a sample of neoplastic cells from the animal; (2) determining a level of S897-EphA2 phosphorylation in the sample; and (3) comparing the determined level of S897-EphA2 phosphorylation in the sample to a control value. An increased level of S897-EphA2 phosphorylation compared to the control value is indicative of malignant progression of the neoplastic cells in the animal.

Samples for use in the methods of the present invention may be obtained from the animal by various well known methods. The animal contemplated by the present invention can be a mammal. In particular aspects of the invention, the animal is a human. A sample obtained from an animal can refer to a biological sample, which includes, but is not limited to a tissue biopsy or section, blood sample, lavage, swab, scrape, nipple aspirate, or other composition that may be extracted from the body and that contains suspected cancer cells. In one particular aspect of the present invention, the tumor sample includes cancer cells, which express EphA2. In some aspects of the invention, the tumor sample contains all or part of a tissue biopsy. In additional aspects of the invention, the samples can include or be entirely comprised of purified proteins or cell lysates.

The neoplastic cells (e.g., cancer cells and/or tumor cells) obtained from the animal can include cancerous cells of the breast, lung, ovary, brain, gastrointestinal tract, salivary duct, endometrium, prostate, head & neck, glioma, pancreas, hepatocyte, myeloma, soft tissue sarcoma, or non-small cell lung cancer, but is not limited to such. In one aspect of the present invention, the cancer cells can be glioma cells. The term glioma, as used herein, refers to a type of cancer arising from glial cells in the brain or spine. Gliomas as contemplated by the present invention can be classified by cell type, by tumor grade, and/or by location. For example, ependymomas resemble ependymal cells, astrocytmoas (e.g., glioblastoma multiforme) resemble astrocytes, oligodedrogliomas resemeble oligodendrocytes. Also mixed gliomas, such as oligoastrocytomas may contain cells from different types of glia. Gliomas can also be classified according to whether they are above or below a membrane in the brain called the tentorium. The tentorium separates the cerebrum, above, from the cerebellum, below. A supratentorial glioma is located above the tentorium, in the cerebrum, and occurs mostly in adults whereas an infratentorial glioma is located below the tentorium, in the cerebellum, and occurs mostly in children.

Certain aspects of the present invention include the step of detecting a level of phosphorylated S897-EphA2 in the sample obtained from the animal. The term "detecting" is used according to its ordinary and plain meaning to refer to "determining the presence of." In certain embodiments, S897-EphA2 phosphorylation is detected by assaying (measuring) a level or amount of phosphorylated S897-EphA2 in a given sample.

Methods of detecting a level S897-EphA2 phosphorylation can be achieved by immunoassay techniques, such as immunoprecipitations, Western blotting, ELISAs, other sandwich assays, FACS analysis and cross-linking assays. In these cases, antibodies may be used in a variety of detection techniques. It is understood that antibodies can be used to detect and to quantify polypeptides.

In some cases, the antibody is an S897-EphA2 targeting agent, while in others, it is used to indirectly evaluate, assess, or determine S897-EphA2 phosphorylation. In particular aspects of the invention, anti-pS897-EphA2 antibodies can be used in the detection of phosphorylated S897-EphA2. Such antibodies, polyclonal or monoclonal, can be generated by those having skill in the art. Detailed methods of antibody production have been described in the Example. Antibodies may also contain a detectable moiety in order visualize bound antibody as needed. Detection of a level of S897-EphA2 phosphorylation may involve labels, tags, colorimetric indicators including fluorescence, enzyme indicators, radioactivity, or other means to quantify or characterize such levels or amounts.

The level of S897-EphA2 phosphorylation detected in a sample can be compared with a control value or control level to correlate malignant tumor progression of the tumor cells obtained from the animal. The control value or control level can be the level of S897-EphA2 phosphorylation in a nonmetastatic cell or in cancer cells with S897-EphA2 phosphorylation at levels similar to that in a normal cell (considered normal S897-EphA2 phosphorylation levels). An animal whose cancer cells have a level of S897-EphA2 phosphorylation that is greater than S897-EphA2 phosphorylation in a non-metastatic cell or in cancer cells with S897-EphA2 phosphorylation at levels similar to that in a normal cell (considered normal S897-EphA2 phosphorylation levels) can be indicative of a malignant tumor.

It is contemplated that one or more standards may be generated in which a control value or level is defined by a normal level of S897-EphA2 phosphorylation. That standard may then be referred to as a way of determining whether S897-EphA2 phosphorylation in a given sample taken from an animal is normal or above-normal. The type of standard generated will depend upon the assay or test employed to evaluate S897-EphA2 phosphorylation. In some embodiments of the invention, a score is assigned to a sample based on certain criteria and numbers within or above a certain number or range are deemed "above normal."

In some aspects of the invention, S897-EphA2 phosphorylation is considered above normal if an assay indicates that a particular measurement, amount or level is at about or at least about 80%, 75%, 70%, 65%, 60%, 55%, 50%, 45%, 40%, 35%, 30%, 25%, 20%, 15%, 10%, 5% or greater than the measurement, amount or level observed in cells or samples that have normal levels of S897-EphA2 phosphorylation. In other words, for example, a cell with normal S897-EphA2 phosphorylation exhibits a level of S897-EphA2 phosphorylation that is x; the sample from the animal being tested may be 1.5×, in which case, in some embodiments that animal's sample may be considered to have an above normal level of S897-EphA2 phosphorylation.

Alternatively, in some aspects of the invention, S897-EphA2 phosphorylation is considered above normal if an assay indicates that a particular measurement, amount or level is about or at least about 1, 2, 3, 4, 5, 6, 7, 8, 9, 10 or more standard deviations above the measurement, amount or level observed in cells that have normal levels of S897-EphA2 phosphorylation. In other cases, S897-EphA2 phosphorylation may be considered above normal if a measurement, amount or level indicative of S897-EphA2 phosphorylation is or is at most 2, 3, 4, 5, 6, 7, 8, 9, 10, 15, 20, 25, 30, 35, 40, 45, 50 or more times more than the measurement, amount, or level indicative of S897-EphA2 phosphorylation in normal cells.

In some aspects of the present invention, increased levels of S897-EphA2 phosphorylation can be correlated to advanced degrees of tumor progression or even correlated directly to a specific tumor grade when compared to a control level or value. In one particular example, gliomas are can be categorized according to their tumor grade, which may be correlated to the S897-EphA2 phosphorylation level detected in the tumor sample. Low-grade gliomas are typically defined as well-differentiated benign gliomas, whereas high-grade gliomas are malignant gliomas and are recognized as undifferentiated or anaplastic. High-grade gliomas are highly-vascular tumors and have a tendency to infiltrate. They have extensive areas of necrosis and hypoxia. On the other hand, low-grade gliomas grow slowly, often over many years, and can be followed without treatment unless they grow and cause symptoms. Another example of a tumor grading system in which phosphorylated S897-EphA2 may be correlated to, is the World Health Organization grading system for astocytoma. The WHO system assigns a grade from 1 to 4, with 1 being the least aggressive and 4 being the most aggressive. It is contemplated by the present invention that a greater level of S897-EphA2 phosphorylation compared to a control value will correspond to a more advanced tumor progression or even a higher or more malignant tumor grade.

Another aspect of the present invention relates to the inhibition of the PI3K/Akt pathway by a PI3K inhibitor that reduces phosphorylation of EphA2 at Akt substrate site S897. Sufficient activation or inhibition of components of the RTK/PI3K/PTEN/Akt/mTOR pathway by cancer therapeutics can decrease phosphorylation of S897-EphA2. Multiple growth factors (e.g., EGF, PDGF, HGF, and bFGF) stimulate S897 phosphorylation of EphA2. EphA2 agonists, Akt inhibitors, serine/threonine phosphatases (e.g., PP2A), PI3K inhibitors, and PTEN promoters, decrease the level of S897-EphA2 phosphorylation.

Thus, it is contemplated that phosphorylated S897-EphA2 can serve as a surrogate marker of therapeutic efficacy for agents targeting various components of in RTK/PI3K/PTEN/Akt/mTOR pathways. Since lower levels of S897-EphA2 phosphorylation are indicative of lower degrees of tumor progression, it is contemplated by the present invention that a cancer therapeutic which can lower the level of S897-EphA2 phosphorylation in cancer cells is an effective cancer therapeutic.

Therefore, in another aspect of the present invention, a method of determining the efficacy of a cancer therapeutic which affects at least one component of the RTK/PI3K/PTEN/AKT/mTOR pathway in treating a cancer is provided. The method includes: (1) administering a therapeutic agent to the animal; (2) obtaining a tumor sample from the animal; (3) determining a level of pS897-EphA2 in the sample; and (4)

comparing the detected level of pS897-EphA2 in the sample with a control sample level. According to the present invention, a reduced level of pS897-EphA2 in the sample compared to the level of pS897-EphA2 in the control sample is indicative of an effective cancer therapeutic or an effective combination of cancer therapeutics. In certain aspect of the invention, the method includes administering the cancer therapeutic to an animal prior to obtaining a tumor sample from the animal.

Alternatively, the level or amount of S897-EphA2 phosphorylation in a particular cancer cell may already be known, and consequently, that level or amount would be evaluated to make a determination regarding efficacy of a cancer therapeutic in certain aspects of the invention. Specifically, the level of S897-EphA2 indicates the activation of RTK/PI3K/PTEN/Akt/mTOR pathway. This information is then used to select for patients who are likely to respond to therapeutics targeting directly or indirectly components in the RTK/PI3K/PTEN/Akt/mTOR pathway.

A "cancer therapeutic", as used herein, is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting invasion, migration, spreading, or progression of cancer, or increasing the lifespan of an animal with cancer. Anti-cancer agents include biological agents (biotherapy), chemotherapy agents, and radiotherapy agents.

When administered to an animal, the cancer therapeutic can be administered as a pharmaceutical composition comprising a pharmaceutically acceptable carrier. Pharmaceutically acceptable carriers are well known in the art and include, for example, aqueous solutions such as water or physiologically buffered saline or other solvents or vehicles such as glycols, glycerol, oils or injectable organic esters. A pharmaceutically acceptable carrier can contain physiologically acceptable compounds that act, for example, to stabilize or to increase the absorption of the active therapeutic compound. The physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

A pharmaceutical composition can be administered to a subject by various routes including, for example, oral administration; intramuscular administration; intravenous administration; anal administration; vaginal administration; parenteral administration; nasal administration; intraperitoneal administration; subcutaneous administration and topical administration. This may be achieved by administering a single composition or pharmacological formulation that includes one or more cancer therapeutics, or by administering to the animal one or more compositions or formulations, at the same time.

In another aspect of the present invention, a method of screening agents that affect at least one component of the receptor RTK/PI3K/PTEN/AKT/mTOR pathway in a cell is provided. The method includes: (1) administering an agent to a cell expressing EphA2; (2) detecting the level of pS897-EphA2 in the cell; and (3) comparing the detected level of pS897-EphA2 in the cell to a control value or level. It is contemplated by the present invention that either an increased level of pS897-EphA2 in the cell or a decreased level of pS897-EphA2 in the cell compared to the control is indicative of an effective agent. For example, an agent may increase the level of pS897-EphA2 in a cancer cell as a result of increasing Akt or PI3K kinase activity. In another example, an effective agent may decrease the level of pS897-EphA2 by increasing PTEN activity.

A further aspect of invention relates to a method of modulating cell migration (e.g., neoplastic cell migration) in a subject by administering an agent that affects the level of S897-EphA2 phosphorylation in the cell. Using cell migration assays, it was found that the number of migrating cancer cells correlated with the degree of S897 phosphorylation and Akt activation in the cells. In addition, agents that affect the level of S897-EphA2 phosphorylation in a cell can also affect the chemotaxis of cancer cells.

Therefore, in another aspect of the present invention, a method of screening agents that inhibit EphA2 cell chemotaxis is provided. The method includes: (1) administering an agent to a cell expressing EphA2; (2) detecting the level of pS897-EphA2 in the cell; and (3) comparing the detected level of pS897-EphA2 in the cell to a control level. It is contemplated that a lower level of p897-EphA2 in the cell after administration of an agent compared to the control is indicative of an effective agent.

The invention can be used with respect to any agent that affects (e.g., reduces, inhibits, eliminates, or ameliorates) the phosphorylation of S897-EphA2. As used herein, the term S897-EphA2 includes a full-length and a portion of a S897-EphA2 polypeptide such as a ligand-binding domain. Such agents may work by indirectly affecting phosphorylation of S897-EphA2 (e.g., an Akt inhibitor) or they may work directly by affecting S897-EphA2 phosphorylation (e.g., a small peptide, a small molecular weight compounds, or an anti-S897-EphA2 antibody binding to the Akt substrate motif of EphA2).

Agents that can be used in accordance with the present can include or affect at least one of the following activities: bind to S897-EphA2, inhibit S897 phosphorylation of EphA2, inhibit phosphorylation of S897 by Akt, inhibit Akt phosphorylation, and/or suppress or inhibit signaling of the RTK/PI3K/PTEN/AKT/MTOR pathway. Without being bound by theory, an agent identified by the subject screening methods as having one or more of the desired activities may work via any one of a number of mechanisms.

Agents screened can include nucleic acids, peptides, proteins, antibodies, antisense RNAs, RNAi constructs (including siRNAs), DNA enzymes, ribozymes, morpholino constructs, chemical compounds, and small organic molecules. Agents may be screened individually, in combination, or as a library of agents. Agents to be screened in the methods of the present invention can be produced, for example, by bacteria, yeast or other organisms (e.g., natural products), produced chemically (e.g., small molecules, including peptidomimetics), or produced recombinantly. In one particular aspect of the invention, the phosphorylated S897-EphA2 targeting therapeutic agent is an anti-S897-EphA2 antibody or biding fragment thereof. In a certain aspect of the invention, the test agent is a small organic molecule having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems may be developed with purified or semi-purified proteins or with lysates, are often preferred as "primary" screens in that they can be generated to permit rapid development and relatively easy detection of an alteration in a molecular target which is mediated by a test agent. Moreover, the effects of cellular toxicity and/or bioavailability of the test agents can be generally ignored in such a system, the assay instead being focused primarily on the effect of the agent.

A primary screen can be used to identify agents that are more likely to have an effect on tumor progression due to S897-EphA2 phosphorylation, in vitro and/or in vivo. Such a screen for use in the present invention may include a biochemical assay measuring S897-EphA2 phosphorylation. To further illustrate, a biological sample including a cancer cell or cancer cell lysate may be contacted with one or more agents (e.g., individual candidate agents, combinations of two or more agents, a library of nucleic acids, polypeptides, small organic molecules, chemical compounds, etc.) and the ability of the agent to inhibit phosphorylation of S897-EphA2 can be measured and compared to a control sample. One or more agents which decreases the S897-EphA2 phosphorylation level, in comparison to the S897-EphA2 phosphorylation level in the absence of the one or more agents, is a candidate agent for use in the subject methods. Similarly, an EphA2 polypeptide may be contacted with one or more agents (e.g., individual candidate agents, combinations of two or more agents, a library of nucleic acids, polypeptides, small organic molecules, chemical compounds, etc.) and the ability of the agent to decrease the S897 phosphorylation level of an EphA2 polypeptide can be measured.

The efficacy of the agent can be assessed by generating dose response curves from data obtained using various concentrations of the test agent. Moreover, a control assay can also be performed to provide a baseline for comparison. Such candidates can be further tested for efficacy in inhibiting chemotaxis of cancer cells in vitro, spreading, invasion, or migration of cancer cells in vitro, for efficacy in tumor growth, progression, or spreading in vitro or in vivo. For example, the efficacy of the agent can be tested in vivo in any animal cancer models.

In addition to assays, such as described above, the invention further contemplates the generation of cell-based assays for identifying agents having one or more of the desired anti-tumor progression activities. Cell-based assays may be performed as either a primary screen, or as a secondary screen to confirm the activity of agents identified in a cell free screen, as outlined in detail above. Such cell based assays can employ any cell-type expressing EphA2 protein. Exemplary cell types include cancer cell lines, primary tumor xenoplant cultures, and Glioma cells. Cells in culture are contacted with one or more agents, and the ability of the one or more agents to inhibit cell migration/invasion is measured. Agents that inhibit cell migration/invasion are candidate agents for use in the subject methods of inhibiting tumor progression. For example, the identified compounds can be tested in glioma cancer models known in the art.

It has also been discovered by the inventors that one may correlate a level of S897-EphA2 phosphorylation directly to a level of Akt phosphorylation. It is shown in the working example below that, pS897-EphA2 spatially colocalizes with the active Akt in human GBM. It has been shown that EphA2 and Akt constitute a reciprocal regulatory loop whereby Akt phosphorylates unligated EphA2 on S897 to promote cell migration and invasion. Thus, the phosphorylation level of Akt in a cell can be determined or analyzed using a detected level of pS897-EphA2 in a cell.

Therefore, the present invention provides a method of measuring Akt phosphorylation in a cell. The method includes: (1) administering an anti-pS897 antibody or binding fragment thereof to the cell; (2) measuring the level of bound anti-body or fragment thereof in the cell; and (3) correlating the level to an amount of Akt phosphorylation in the cell. Furthermore, any method used or discussed herein with respect to the detection of pS897-EphA2 in cancer cells may be implemented with respect to the detection of Akt phosphorylation.

The anti-pS897 antibody can be polyclonal or monoclonal antibody. Epitope-binding fragments such as Fab, Fab', F(ab)2, Fh, or Fv fragments are included within the scope of this invention. In certain aspects of the invention, the antibodies are fully characterized with respect to the amino acid sequences of both their light and heavy chain variable regions, the cDNA sequences of the genes for the light and heavy chain variable regions, the identification of their CDRs (complementarity-determining regions), the identification of their surface amino acids, and means for their expression in recombinant form (e.g., a hybridoma).

As discussed above, pS897-EphA2 can be directly correlated to phosphorylation of Akt in a cell. It is contemplated by the present invention that one can determine the progress of a disorder associated with aberrant Akt phosphorylation in an animal by determining the level of Akt phosphorylation in the cell. Therefore, in another aspect of the present invention a method of measuring the progress of a disorder associated with aberrant Akt phosphorylation in an animal is provided. The method includes: (1) obtaining a biological sample from an animal; (2) detecting a level of pS897-EphA2 in the sample; and (3) correlating the detected level of pS897-EphA2 in the sample to the progress of a disorder associated with aberrant Akt phosphorylation in an animal. The level of pS897-EphA2 in a sample can be directly correlated to the progress of a disorder associated with aberrant Akt phosphorylation using standards or controls as described above. In a certain aspect of the invention, an increased level of pS897-EphA2 in a sample compared to a control would indicate greater progression of a given disorder.

Many disorders are characterized by or caused by aberrant phosphorylation of Akt in animals cells. An example of a disorder is cancer. Particular examples of cancer include breast cancer, lung cancer, ovarian cancer, endometrial cancer, uterine cancer, brain cancer, sarcoma, melanoma, glioblastoma, leukemia, lymphoma, colorectal cancer, prostate cancer, pancreatic cancer, renal cell cancer, and liver cancer. The most dangerous progression states are malignant progression states, which give the cell the ability to spread, either by direct growth into adjacent tissue through invasion, or by implantation into distant sites by metastasis. Metastatic cells have acquired the ability to break away from the primary tumor, translocate to distant sites through the bloodstream or lymphatic system, and colonize distant and foreign microenvironments. Examples of other disorders characterized by or caused by aberrant phosphorylation of Akt in an animal's cells can include rheumatologic disease, e.g., rheumatoid arthritis or osteoarthritis. A further example of a disorder is pulmonary disease, e.g., chronic obstructive pulmonary disease (COPD).

It has been shown that S897-EphA2 is over phosphorylated in a number of neoplasm types, including cancers. The inventors have discovered that Akt phosphorylated EphA2 is preferentially targeted to the migrating front of tumor cells which is required to promote assembly of active cytoskeleton and extension of lamellipoida. Thus, S897-EphA2 phosphorylation can be targeted in an effort to inhibit cell migration and invasion.

Therefore, in another aspect of the invention, a method of inhibiting neoplastic cell migration, invasion, and/or spreading is provided. The method includes administering to a neoplastic cell expressing EphA2, an effective amount of an agent that targets S897-EphA2 and inhibits phosphorylation of S897 of EphA2. In certain aspects of the invention, the neoplastic cell is a cancer cell expressing EphA2. In one example, the methods of the present invention can inhibit the migration of metastatic cancer cells expressing EphA2, particularly those expressing overly phosphorylated S897-EphA2.

It is understood that the term "overly phosphorylated S897-EphA2 cancer cells" refers to a cancer cells whose etiology or cause is believed to be related to higher levels of S897-EphA2 phosphorylation compared to noncancerous cells, non-malignant cancer cells, or cancer cells whose etiology or cause is not related to S897-EphA2 phosphorylation levels.

The agent that targets S897-EphA2 and inhibits phosphorylation of S897 of EphA2 can include but is not limited to an antibody or binding fragment thereof, a small molecule, a peptide, a polypeptide, or any of the agents screened by the methods of the present invention. In one example, the agent can include an anti-pS897-antibody or binding fragment thereof as described above.

Certain aspects of the invention provide a combination or multiple agents that target S897-EphA2 for inhibiting neoplastic cell migration and invasion. Additionally, the subject methods may be used in combination with other anti-cell migration and invasion therapeutic agents, including, but not limited to, anti-cancer agents.

In certain aspects of the invention, administering an S897-EphA2 targeting agent can include contacting the cell with an S897-EphA2 targeting agent. The effective amount of an S897-EphA2 targeting agent can readily be determined by one skilled in the art. In certain aspects of the invention, the effective amount of an S897-EphA2 targeting agent administered to the cell can be any amount that measurably inhibits cell migration and invasion. Various cell migration assays known in the art can readily be used to determine an effective amount.

Example

Both pro- and anti-oncogenic properties have been attributed to EphA2 kinase. We found that a possible cause for this apparent paradox is the diametrically opposite roles of EphA2 in regulating cell migration and invasion. While activation of EphA2 with its ligand ephrinA1 inhibited chemotactic migration of glioma and prostate cancer cells, EphA2 overexpression promoted migration in a ligand-independent manner. Surprisingly, the latter effects required phosphorylation of EphA2 on serine 897 by Akt, and S897A mutation abolished ligand-independent promotion of cell motility. EphrinA1 stimulation of EphA2 negated Akt activation by growth factors and caused EphA2 dephosphorylation on S897. In human astrocytoma, S897 phosphorylation is correlated with tumor grades and Akt activation, suggesting that the Akt-EphA2 crosstalk may contribute to brain tumor progression.

Akt is frequently activated in human glioblastoma and prostate cancer due to loss of PTEN or activation of components in PI3K/Akt pathway. We found that EphA2 is both an upstream negative regulator and a downstream effector of Akt. Phosphorylation of EphA2 on S897 by Akt promotes cell migration and invasion. In contrast, EphA2 stimulation by ephrinA1 ligand suppresses Akt activation and inhibits cell migration. Thus, activation of PI3K/Akt pathway coupled with the loss of ephrinAs convert EphA2 kinase from a tumor suppressor into a partner with Akt in promoting malignant progression. The data have important implications in developing therapeutic strategies targeting EphA2 for treatment of malignant tumors where PI3K/Akt pathway is activated.

We found that EphA2 exerts diametrically opposite effects on chemotactic cell migration: while overexpression of EphA2 promotes chemotactic cell migration in a ligand-independent manner, ligand stimulation of EphA2 significantly suppresses it. EphA2 and Akt constitute a reciprocal regulatory loop whereby Akt phosphorylates unligated EphA2 on S897 to promote cell migration and invasion, whereas ligand-activated EphA2 negatively regulates Akt, strips S897 phosphorylation and suppresses cell migration and invasion. Moreover, staining with an antibody against the S897-phosphorylated EphA2 revealed that Akt-mediated phosphorylation EphA2 is correlated with malignant progression of brain tumors.

Ligand-Independent Stimulation and Ligand-Dependent Inhibition of Cell Migration by EphA2 Kinase We investigated how EphA2 overexpression may regulate chemotactic cell migration and invasion in the absence and presence of its ligand ephrinA1 using glioma cells as a model system. EphA2 is frequently overexpressed in GBM with concomitant loss of endogenous ligand expression. Examination of public microarray database also revealed overexpression of EphA2 at mRNA levels in GBM. To mimic the in vivo situation, we overexpressed EphA2 in U373 glioma cells. FIG. 1A shows that U373 cells express moderate levels of endogenous EphA2 (FIG. 1A), and infection with EphA2-expressing retrovirus increased the level by about one fold. In keeping with the lack of ligand expression, both endogenous and ectopic EphA2 in U373 cells showed low basal activation. Stimulation with exogenous ephrinA1-Fc caused rapid EphA2 activation, which was followed by degradation of the receptor itself, characteristic for most RTKs including Eph kinases. In a Boyden chamber cell migration assay using serum as a chemoattractant, we found that overexpression of EphA2 alone, in the absence of ligand stimulation, significantly enhanced serum-induced migration of U373 cells (FIG. 1B). In contrast, activation of EphA2 with its ligand ephrinA1 significantly inhibited the chemotaxis of both vector control and EphA2-overexpressing cells. These data suggest that EphA2 has both ligand-independent stimulatory effects as well as ligand-dependent inhibitory effects on chemotactic cell migration. The diametrically opposite properties of EphA2 kinase in regulating cell migration were also observed in other cell types, including HEK 293, U87, A172 and PC-3 cells.

In a reverse experiment, we tested how down-regulation of EphA2 expression could affect cell motility. ShRNA knocking down of EphA2 expression in U373 cells (FIG. 1C) led to a significant reduction of ligand-independent chemotaxis toward serum (FIG. 1D). The residual EphA2 on U373 cells was still able to mediate inhibition of cell migration upon ligand stimulation (FIG. 1D). Similarly, shRNA knockdown in PC-3 prostate cancer cells significantly reduced basal cell migration (FIG. 1E, F), whereas overexpression of EphA2 promoted chemotaxis.

Extensive previous investigations have established that a major function of Eph kinases is the ligand-dependent repulsion of migrating cells and axons both in vitro and in vivo. Our data demonstrate that EphA2 kinase can also promote cell migration in cooperation with growth factors in a ligand-independent manner.

EphA2 is Both a Downstream Substrate and an Upstream Negative Regulator of Akt

In exploring the molecular mechanisms that mediate ligand-independent promotion of chemotaxis by EphA2, we screened several signaling pathways. Among them, PI3K/Akt pathways stood out by robustly responding to serum in migrating U373 cells. As shown in FIG. 1G, Akt became highly phosphorylated at both T308 and 5473 sites. Cotreatment with ephrinA1 completely blocked Akt activation by serum. To test a possible direct crosstalk between Akt and EphA2 kinases, we precipitated EphA2 and probed it with an antibody that recognized the consensus Akt substrate sites (Akt-pSub). The antibody detected a strong band at 125 kDa on EphA2 precipitates prepared from serum-stimulated cells (FIG. 1H), indicating that EphA2 could be a novel substrate for Akt. To confirm this unexpected finding, immunoprecipitation was performed with AktpSub antibody, and the precipitates were immunoblotted for EphA2. EphA2 could be readily detected in the Akt-pSub immunoprecipitates (FIG. 8A). EphrinA1 cotreatment led to complete inhibition of EphA2 phosphorylation as detected by the Akt-pSub antibody (FIG. 1H), which was correlated with the abolishment of Akt activation as indicated by the lack of phosphorylation at both S473 and T308 sites (FIG. 1G).

To verify the specificity of serum-induced S/T phosphorylation of EphA2 to Akt activity, we performed the same experiments on cells pretreated with PI3K inhibitor, LY294002. Inhibition of PI3K/Akt pathway by LY294002 significantly reduced the phosphorylation of EphA2 at Akt substrate sites in serum-stimulated cells (FIG. 1I). To further demonstrate the Akt-EphA2 crosstalk, dominant negative (DN) Akt was expressed in U373 cells. As shown in FIG. 1J, serum-induced S/T phosphorylation of EphA2 was attenuated by the expression of DN Akt. Taken together, these results identify a reciprocal regulatory loop between EphA2 and Akt: Whereas unligated EphA2 functions as a downstream substrate and effector of Akt kinase, ligand activated EphA2 is an upstream negative regulator to turn off Akt activities.

To examine where Akt-EphA2 crosstalk may take place in migrating cells, we investigated the subcellular localization of EphA2 relative to p-Akt. Freshly confluent U373 cells were serum starved and scratch-wounded to induce cell migration. Two hours later, serum was added alone or together with ephrinA1-Fc. FIG. 1K shows that under serum-starved condition, p-Akt was low and uniformly distributed in cells with no obvious colocalization with EphA2 (FIG. 1K, top panels). Within 10 min after serum treatment, p-Akt was upregulated and became colocalized with EphA2 in lamellipodia at the leading edge (FIG. 1K, middle panels). Cotreatment with ephrinA1 caused retraction of lamellipodia and disappearance of p-Akt from the leading edge. Akt-pSub was also localized at the migrating front together with EphA2, but not at cell-cell junction sites where EphA2 was also present at high levels (FIG. 8B), suggesting that Aktphosphorylated EphA2 is preferentially targeted to migrating front. Costimulation with ephrinA1 and serum caused significant loss of p-Akt from the leading edge (FIG. 1K, bottom panels) together with p-Akt-Sub (FIG. 8B). Thus, in response to growth factor stimulation, the unligated EphA2 is phosphorylated at the leading edge by the active Akt; upon addition of exogenous ligand, EphA2 is activated, leading to "repulsion" of the migrating cells.

Serine 897 of EphA2 is the Major Substrate Site for Akt

Sequence analysis of EphA2 revealed several potential S/T sites that resemble the consensus motif of known Akt substrates (FIG. 2A). To map the Akt phosphorylation site(s) in EphA2, site-directed mutagenesis was carried out to replace all five potential S/T residues with alanine in the cytoplasmic tail. A site in the ectodomain (S479) was also included as a control. The resultant mutants were initially tested in HEK 293 cells. HEK 293 cells express very low levels of endogenous EphA2. Activation of EphA receptor tyrosine kinase inhibits the Ras/MAPK pathway, providing a low background to evaluate the mutants. We first examined how each individual S/T to A mutation of the potential site affected serum-induced phosphorylation of EphA2. In response to serum stimulation, cells expressing wild type EphA2 or EphA2 with single mutation at S479, S636, T795, T838, and S910 were equally phosphorylated at Akt substrate sites. In contrast, S897A mutation rendered EphA2 completely resistant to serum-induced phosphorylation at Akt substrate sites (FIG. 2B). Identical results were obtained from three independent transfections. Therefore, our studies mapped serine 897 as the major site for Akt kinase phosphorylation in EphA2. Serine 897 is located in the linker region between EphA2 kinase domain and sterile α motif (SAM), which is likely to be exposed and accessible to Akt phosphorylation.

Akt-Mediated Serine 897 Phosphorylation is the Major Mechanism Responsible for Ligand-Independent Stimulation of Cell Migration and Invasion by EphA2

To determine the functional significance of phosphorylation at S897, HEK 293 cells expressing wild type-, S897A-EphA2 or control vector were characterized. We also created the phospho-mimetic mutation by replacing S897 with aspartic acid (S897D). Immunofluorescence and biochemical analysis showed that the exogenous WT-, S897A- and S897D-EphA2 were homogenously overexpressed in HEK 293 cells (FIG. 2C, D). We then performed Boyden chamber cell migration assay on the transfected HEK 293 cells. Similar to what we observed in U373 glioma cells (FIG. 1B), overexpression of wild type EphA2 increased serum-induced chemotactic migration of HEK 293 cells (FIG. 2E). Interestingly, both S897A and S897D mutations completely abolished the cell migration-promoting effect by EphA2 (FIG. 2E). These results suggested that Akt phosphorylation of S897-EphA2 is largely responsible for the ligand independent stimulation of cell motility by EphA2 in HEK 293 cells. The fact that phospho-mimetic mutation (S897D) had the same effects as S897A indicates that phosphorylation, but not the negative charge-induced conformational changes is needed to promote cell migration.

The intrinsic tyrosine kinase activities of EphA2 was not required for ligand-independent promotion of chemotaxis, because the kinase deficient D739N mutant of EphA2 was still fully capable of simulating chemotaxis toward serum when overexpressed in HEK 293 cells (FIG. 9). However, the mutant did lose its ligand-dependent inhibition of cell migration.

Ligand-Independent Promotion of Chemotaxis by EphA2 in Glioma and Prostate Cancer Cells Requires S897 Phosphorylation, and is Sensitized by PTEN Deletion Next we investigated the effects of the S897A mutant on ligand-independent chemotactic migration in a panel of human tumor cell lines, including U373, U87, A172, LN229 and T98G glioma cells, as well as PC-3M prostate cancer cells. As expected, the PTEN-null U373, U87, and A172 cells generally have more active Akt than PTEN-wild type T98G and LN229 cells (FIG. 10). Hyperactive Akt was also observed in the PTEN null PC-3M cells (FIG. 11) as well as in parental PC-3M cells. WT and S897A-EphA2 were introduced into these cells via retroviral infection (FIG. 3A, B). Overexpression of WT-EphA2 enhanced serum-stimulated cell migration compared to vector control in PTEN-null U373, U87, A172 and PC-3M cells (FIG. 3C, D). S897A mutation blocked most of the stimulatory effects in these cells. Interestingly, U373 cells expressing S897A-EphA2 displayed lower basal levels of serum-induced chemotaxis than vector control cells. The seemingly dominant negative effects were not observed in U87, A172 and PC-3M cells. The differences among different cell types likely reflect the complexity of signaling networks regulating chemotaxis. We believe that the importance of Akt-EphA2 crosstalk in promoting chemotaxis relative to other signaling pathways is likely to be cell type-dependent, leading to different response to S897A mutant in different cell types. In contrast with PTEN-null cells, T98G and LN229 cells harboring wild type PTEN and lower Akt activities were refractory to the stimulation of chemotaxis by the overexpressed EphA2 (FIG. 3D).

Together these data indicate that PTEN-null cells with hyperactive Akt may have become more dependent on or addicted to Akt-EphA2 crosstalk to promote cell motility. To test this possibility, we restored PTEN expression in U373 cells, which caused a significant reduction in serum-induced Akt activities (FIG. 3E, F). In both chemotactic cell migration and scratch wound assays, restoration of PTEN expression dramatically inhibited cell migration (FIG. 3G, H), supporting important roles of PTEN loss in promoting malignant behaviors of glioma cells. Growth factor-induced chemotactic cell migration involves activation of RTK/PI3K/Akt cascade that is counter balanced by PTEN. It is possible that PTEN may attenuate chemotaxis in part by preventing aberrant PI3K/Akt activation, which in turn keeps Akt-EphA2 signaling axis in check. Loss of PTEN leads to sustained and unregulated Akt hyperactivation, which phosphorylates EphA2 on S897 to promote cell migration. However, other mechanisms in addition to loss of PTEN may also permit EphA2 to promote chemotactic cell migration, since in PTEN-wild type HEK 293 cells EphA2 overexpression is still capable of promoting migration (FIG. 2D). Notably hyperactivation of Akt can be achieved by a variety of mechanisms including loss of PTEN, RTK amplification/mutation, Akt amplification, and Ras activation. Further studies are needed to identify the alternative mechanisms.

Ligand-Dependent Inhibition of Cell Migration by EphA2 is not Affected by S897A Mutation The data from the last section suggest that EphA2 functions as a ligand-independent positive regulator of chemotactic migration in multiple tumor cell lines, which requires Akt-mediated phosphorylation of S897. Next, we investigated how overexpression of S897A-EphA2 might affect ligand-dependent inhibition of cell migration. We focused on U87, U373 and A172 glioma cell lines. The multiplicity of the cell lines with a shared genetic alteration in PTEN deletion makes them good models for assessing general applicability of our findings. Similar to what was found in U373 cells (FIG. 1B), chemotactic cell migration of A172 and U87 cells expressing WT-EphA2 or vector control was significantly inhibited by ephinrA1 (FIG. 4A-C). Interestingly, S897A-EphA2 was still capable of mediating ephrinA1-induced inhibition of migration in all three cell lines, despite its ability to abolish most ligand-independent promotion of cell migration. Indeed, the degrees of ligand-dependent inhibition were indistinguishable between WT- and S897A-EphA2 cells. These results suggest that EphA2-mediated ligand-dependent inhibition of chemotaxis is not a simple reverse of its ligand-independent promotion; but a separate cellular process involving distinct signaling pathways.

Invasion through the surrounding normal tissues is a hallmark of malignant progression, and is particularly deadly for glioblastoma patients. We found that, in the absence of ligand stimulation, overexpression of WT-EphA2 strongly promoted MatriGel invasion of U373, U87 and A172 glioma cells (FIG. 4D-F, open bars). Similar to ligand dependent inhibition of cell migration, ephrinA1 treatment significantly blocked MatriGel invasion, and the percentage of inhibition was comparable between WT- or S897A-EphA2 or vector control cells (FIG. 4D-F). One consistent difference across all three cell lines was that both ligand-independent promotion and ligand-dependent inhibition were more pronounced in the invasion assay than migration assay (FIG. 4A-F). These data demonstrate that EphA2 promotes both cell migration and invasion independent of ligand, and phosphorylation of S897 is required for both effects. On the other hand, ligand-dependent inhibition of cell migration and invasion is independent of S897 phosphorylation.

Time-lapse imaging was employed to monitor cell morphology and chemokinetic movement of cells on two-dimensional culture plate. In keeping with the increased cell motilities in Boyden chamber assay, U373 cells expressing WT-EphA2 displayed elongated and polarized morphology with a large protruding lamellipodium (FIG. 4G), and were more motile compared with vector control cells. In contrast, cells expressing S897A-EphA2 showed a "pancake-like" morphology in culture dishes and were largely stationary during the course of the observation (FIG. 4G).

Multiple Growth Factors Stimulate S897 Phosphorylation of EphA2

To better understand the function of S897 phosphorylation of EphA2, we generated and characterized a rabbit polyclonal antibody against a synthetic phosphopeptide surrounding S897 (Methods). We validated the phospho-specific antibody in HEK 293 cells expressing WT- or S897A-EphA2 or vector control. Immunoblot of cell lysates with the antibody detected strong signals at the same molecular weight as EphA2 in the serum-stimulated WT-EphA2-expressing cells, but not in cells expressing the unphosphorylatable S897A-EphA2 (FIG. 5A). Costimulation with serum and ephrinA1-Fc abolished the pS897-EphA2 signal. A robust pS897 band co-migrating with EphA2 was also detected in EphA2 immunoprecipitates (FIG. 5B). Conversely, EphA2 was detected in the materials precipitated with the anti-pS897-EphA2 antibody (FIG. 12). Treatment with recombinant serine/threonine protein phosphatase 2A (PP2A) eliminated the signal (FIG. 5C). Finally treatment of cells with SH-5, an Akt inhibitor, suppressed S897 phosphorylation (FIG. 5D); so did LY294002, an inhibitor of PI3K (FIG. 13). Taken together, this series of experiments confirmed specificity of the antibody. They also further established EphA2 as an effector molecule for PI3K/Akt signaling cascade.

To determine which growth factors induce phosphorylation of EphA2 on S897, we stimulated U373 glioma cells with a panel of growth factors including EGF, bFGF, PDGF, and HGF, which have all been implicated in development of human GBM. Serum was used as a positive control. We found that all growth factors were capable of inducing pS897-EphA2, which was correlated with Akt activation (FIG. 5E). In cell migration assays, all four growth factors were potent chemoattractants for U373 cells (FIG. 5F). The number of migrating cells correlated with the degree of S897 phosphorylation and Akt activation with stronger chemotaxis by HGF and EGF. Costimulation of cells with ephrinA1-Fc significantly inhibited pS897-EphA2 induced by all growth factors, concomitant with Akt inactivation (FIG. 5E). Chemotaxis was also significantly blocked (FIG. 5F). The degree of ephrinA1-dependent inhibition of Akt varied among different growth factors, with strongest inhibition for bFGF; significant but less inhibition was seen with EGF and HGF that were stronger activators (FIG. 5E). These results suggested that phosphorylation of EphA2 at S897 is a common mediator of growth factor-induced chemotaxis, which could have important implications in understanding the molecular basis of malignant progression for GBM and potentially other tumor types.

LPA in serum is known to activate Akt and induce cell migration as well. However, in U373 cells, LPA is a weaker inducer of Akt activation and chemotactic cell migration, which was not affected by ephrinA1 (FIG. 5E, F). Thus, LPA in serum did not contribute significantly to either Akt activation or S897 phosphorylation in this system. Next, we examined whether kinase activities of the growth factor receptors are required for activation of Akt and phosphorylation of EphA2 on S897. Two inhibitors of FGFR abolished the stimulatory effects of bFGF (FIG. 5G). Although a small decrease was observed, serum-induced activation of Akt and pS897-EphA2 was not significantly reduced by FGFR inhibitors (FIG. 5G), consistent with the presence of multiple growth factors in serum.

Immunofluorescence staining of U373 expressing WT-EphA2 using the phosphospecific antibody revealed that pS897-EphA2 was localized to the migrating front with dentritic actin in lamellipodia or tips of F-actin fibers that ran perpendicular to the wound (FIG. 5H). As expected, cells expressing mutant S897A-EphA2 showed little staining for phospho-S897 (FIG. 5H, lower panel). Staining for total EphA2 showed that the mutant S897A-EphA2 was primarily localized to the cell-cell junctions instead (FIG. 5I). Interestingly, prominent actin stress fibers were detected in cells expressing mutant S897A-EphA2 that ran parallel to the wound (FIG. 5H, I). This is analogous to rearrangement of F-actin following stimulation with ephrinA1, that caused F-actin to switch from predominantly dendritic pattern in lamellipodia to stress fibers that aligned with the direction of wounding (FIG. 14). These results suggest that phosphorylation of EphA2 at S897 by Akt is critical for EphA2 localization at cell leading edge, which is required to promote assembly of actin cytoskeleton and extension of lamellipodia.

S897 phosphorylation of EphA2 is Correlated with Malignant Progression and Overlaps With Active Akt in Human Astrocytoma PI3K/Akt is activated in the vast majority of human GBM. Comprehensive genomic characterization defines human glioblastoma genes and core pathways, and glioma cells induced to migrate are known to have further elevated Akt activities. We hypothesize that if Akt phosphorylation of S897-EphA2 facilitates glioma cell migration in vitro, S897 phosphorylation of EphA2 could be elevated during malignant progression of human brain tumors in vivo. To test this, we performed immunohistochemistry on paraffin-embedded sections from normal human brains and human gliomas of different grades using the phospho-specific antibody characterized above. Confirming the specificity of the antibody in IHC staining, the pS897 signals on adjacent sections of the same grade IV GBM could be blocked by the immunizing phospho-peptide but not the unphosphorylated peptide (FIG. 6A-D). As shown in FIG. 6, normal brains from five individuals were largely negative for pS897-EphA2 (FIG. 6E, F), whereas one case of grade I (FIG. 6G, H) and two cases of grade III astrocytomas (FIG. 6I, J) showed low to moderate pS897-EphA2 levels. In contrast, 19 of 21 cases of grade IV astrocytomas (GBM) samples contained regions displaying high levels of pS897-EphA2 (FIG. 6K-T). The areas affected varied among different tumors, comprising 5% to over 90% of tumor sections of the non-necrotic regions.

Interestingly, the strongest staining for pS897-EphA2 was frequently localized in regions known to be enriched for growth factors and invasive cells in grade IV astrocytomas. Clusters of strongly positive tumors cells were often observed next to necrotic areas, one of the WHO-designated hallmarks of grade IV astrocytomas (FIG. 6K). The distinctive membrane staining pattern of pS897-EphA2 could be visualized in the high magnification images (FIG. 6L). Phospho-S897-EphA2 was also abundantly detected in the perivascular regions (FIG. 6M, N), or at the interface between vasculature and necrosis (FIG. 6O). Invasive glioma cells often migrate along blood vessels, which is referred to as perivascular satellitosis, one of morphological signatures of invasive GBM collectively known as Scherer's secondary structures. Phospho-S897-EphA2 was also detected in a tumor that has infiltrated meninges adjacent to normal brain (FIG. 6P), further supporting its role in promoting tumor cell migration. On multiple sections, pS897-EphA2 was found at high levels in cells comprising palisading necrosis (FIG. 6QS). In GBMs, necrotic foci are often surrounded by pseudopalisading cells. These pseudopalisading tumor cells are thought to be actively migrating and are critical for tumor progression. Pseudopalisades in glioblastoma are hypoxic, express extracellular matrix proteases, and are formed by an actively migrating cell population. Neuropathology for the neuroradiologist: palisades and pseudopalisades. Finally, pS897-EphA2 was found in microvascular proliferation resulting from active angiogenesis in GBM (FIG. 6T), suggesting that pS897-EphA2 could also play a role in promoting endothelial cell migration and invasion during neo-angiogenesis.

One prediction based on our data is that pS897-EphA2 is likely to co-localize with the activated Akt in the same tumor regions. To examine this possibility, we stained the same set of GBM specimens for pS473-Akt. The pS473-Akt signal was weaker than pS897-EphA2 in about a third of the specimens, possibly due to differences in antibodies or more labile nature of the pS473-Akt epitope. Interestingly, in most regions where there was strong pS473-Akt, there was also robust staining for pS897-EphA2 on adjacent sections (FIG. 6V-X). The spatial colocalization was most pronounced in tumor cells surrounding blood vessels (FIG. 6 V, W on adjacent slides with FIG. 6M.N) or necrotic regions (FIG. 6X). Taken together, the results demonstrate that phosphorylation EphA2 on S897 by Akt is correlated with malignant progression of human astrocytoma.

We report here that EphA2 kinase has diametrically opposite roles in regulating chemotactic cell migration: ligand-independent promotion and ligand-dependent inhibition. We characterized a reciprocal regulatory loop between EphA2 and Akt, in which unligated EphA2 is a substrate for Akt; Akt in turn is negatively regulated by the ligand-activated EphA2 (see FIG. 7). We further demonstrate that phosphorylation of a single serine residue, S897, by Akt is responsible for ligand-independent promotion of cell migration and invasion by EphA2, which becomes dephosphorylated upon ligand stimulation. The ligand-dependent inhibition and ligand-independent stimulation of cell migration and invasion may represent one possible mechanism responsible for the hitherto seemingly conflicting roles attributed to EphA2 in tum-origenesis. Our data also suggest that EphA2 is an important effector molecule of Akt in promoting malignant progression of brain and prostate cancer, making it an attractive target for therapeutic intervention.

Ligand-Independent and -Dependent Functions of EphA2 Utilize Distinct Mechanisms The ligand-independent S897 phosphorylation of EphA2 seems to primarily affect cell motility as it did not affect cell growth and survival in vitro (not shown) or intracranial growth in vivo (FIG. 15). How EphA2 may promote cell migration/invasion in cooperation with Akt at the molecular level is currently unclear, although there are a few hints. For a cell to migrate, it must become polarized. An interesting observation in this study is that cells expressing wild type EphA2 are more polarized compared with cells expressing mutant S897A-EphA2 or vector control. Moreover, phospho-S897-EphA2 was detected at leading edge and tips of stress fibers near cell front in cells expressing WT-EphA2. These data indicate that Akt phosphorylation of EphA2 at S897 is critical for polarized localization of EphA2 and actin polymerization. The lack of lamellipodia structure in S897A-EphA2-expressing cells suggested that accumulation of EphA2 at leading edge may play an instructive role in lamellipodium protrusion.

The ligand-independent promotion and ligand-dependent inhibition of cell migration by EphA2 apparently utilize distinct signaling pathways, because migration of cells expressing S897A-EphA2 could still be inhibited upon ephrinA1 stimulation, although it could no longer promote cell migration. In PC-3 cells, EphA2 kinase activation inhibits integrin signaling and integrin-mediated haptotactic cell migration. We found here that ephrinA1 stimulation significantly reduced β1-integrin localization to leading edge in migrating glioma cells (FIG. 14), indicating that inhibition of integrin function may be one of the contributing mechanisms for ligand-dependent suppression of cell motility by EphA2 kinase.

EphA2-Akt Crosstalk in Brain Tumors and its Clinical Implications

GBM is the most common primary brain tumors. The dismal prognosis of these tumors, with an average survival of less than a year, is attributable to difficulties in early detection, and to widespread brain invasion at the time of diagnosis. Extensive molecular studies have identified several signaling pathways implicated in the etiology and progression of GBM. PI3K/Akt signaling pathway is among the most frequently altered pathways. Activation of upstream RTK growth factor receptors and/or loss of the negative regulator, PTEN, are the major causes for PI3k/Akt activation, particularly in primary GBM. Recent studies show that multiple growth factor receptors, including EGFR, PDGFR, and MET are simultaneously or sequentially activated in GBM, and seem to be required for maintaining downstream pathway activation. Coactivation of receptor tyrosine kinases affects the response of tumor cells to targeted therapies. Science 318, 287-290). We show here that many growth factors including EGF, PDGF, HGF, and bFGF are capable of inducing S897 phosphorylation of EphA2 concomitant with Akt activation. IHC staining demonstrates that significant S897 phosphorylation of EphA2 also occurs in human astrocytoma specimens in vivo. The degree of S897 phosphorylation is correlated with astrocytoma grades, with strongest signals found in regions known to be enriched for invasive malignant tumor cells. Supporting an active crosstalk between EphA2 and Akt in vivo, pS897-EphA2 spatially colocalizes with the active Akt in human GBM.

In glioblastoma, the oncogenic effects of PTEN loss are mediated by increased activation of PI3K/Akt signaling cascade. We demonstrate here that ephrinA1 stimulation of EphA2 preferentially inhibits Akt activation and growth factor-induced migration and invasion in PTEN-deficient glioma cells. We further demonstrate that restoration of PTEN expression reduced migratory and invasive potentials of PTEN-null glioma cells. It is possible that the PTEN-null cells may have become more dependent on EphA2/Akt crosstalk for cell motility, and potentially more susceptible to therapies targeting EphA2. Exploration of EphA2 agonists may represent a feasible approach to converting EphA2 from an oncogenic partner of Akt in promoting cell migration and invasion into a tumor suppressor that repulses invading cells.

The correlation between pS897-EphA2 and malignant progression coupled with the strength and persistence of pS897-EphA2 signal in human cancer suggest that it can be used as a novel marker of tumor progression. Moreover, because inhibitors of growth factor receptors, PI3K, and Akt could all diminish pS897-EphA2, it may serve as a surrogate marker of therapeutic efficacy for agents targeting various components in RTK/Ras/PI3K/Akt pathways.

We found that Akt-mediated phosphorylation of EphA2 also took place in the glioma stem/initiating cells (GSC) (FIG. 16). As the name indicate, GSC are that give rise to tumor mass and confer resistance to therapy. GSC 1228 and 827 cells were cultured in suspension (A,C) and on laminin (B,D). The 1228 line of GSC cells were plated on laminin and subjected to immunofluorescent analysis for Nestin (E) and EphA2 (F). Which were merged with DAPIin (G). (H) A fraction of 1228 GSC cells also express GFAP, a differentiation marker. (I) EphA2 in 1228 cells was phosphorylated on S897 in the absence of ligand stimulation. Ephrin-A1 treatment led to EphA2 activation, and inhibition of Akt and pS897-EphA2. (J) EphA2 shRNA knockdown inhibited chemotactic migration of GSC cells toward to EGF and bFGF. n-s shRNA: non-silencing shRNA.

Expression of mutant EphA2, where the serine 897 was converted to alanine (S897A), greatly reduced the invasion of GSC after intracranial implantation (FIG. 18). Please note, GSC cells are capable of "diffuse invasion" inside the brain, a lethal hallmark of human malignant glioma. In contrast, most of the conventional established cell lines commonly used in glioma research do not invade inside the brain. GSC are becoming preferred model to study brain tumor biology.

FIG. 17 shows pair-wise comparison strategy to evaluate the role of Akt-mediated phosphorylation of EphA2 on serine 897 (S897) on in vivo invasion of human GSC cells upon intracranial injection. GSC cells expressing WT- or S897A-EphA2 are used as an example. The two cell populations will be tagged with either GFP or mCherry. They will be mixed at 1:1 ratio and co-injected intracranially into SCID mice. This strategy enables direct comparison between different mutants. For example, S897A mutant is expected to reduce invasion.

FIG. 18 shows S897 a mutation of EphA2 retarded diffuse invasion of glioma progenitor/stem cells (GSC) in NOD/SCID mouse brain suggesting an essential role of Akt-EphA2 crosstalk in glioma invasion in vivo. Pair-wise comparison was performed as described in FIG. 17. A) Briefly, two populations of GSC cells (line827) were co-injected at 1:1 ratio intracranially into NOD/SCID mice. One population expressed WT-EphA2 and was tagged with GFP; another expressed S897A-EphA2 and was tagged with mCherry. B-G) Three weeks after injection, mice were sacrificed and subject to whole body perfusion with 3.7% paraformaldehyde (PFA). Brains were dissected and further fixed for 2 hours. The entire brains were immediately imaged on a fluorescent microscope. Scale Bar: 100 μm.

Please note the following: 1) At the site of injection, merged image shows that there were equivalent number of GFP- and mCherry-pssitive cells, as expected. 2) However, more GFP than mCherry cells had dispersed to distal region of the brain (compare E vs. F). 3) Even single cells can be visualized. Similar data were obtained in three different mice. The slides from the specimens will be analyzed as described in the application to further validate these observations. While still preliminary, the data did prove the feasibility of our innovative pair-wise comparison approaches. More excitingly, they suggest that Akt phosphorylation of EphA2 on S897 may indeed play a critical role in promoting diffuse invasion of GBM in vivo.

Moreover, we discovered that the S897 site phosphorylation by Akt also plays a critical role in supporting tumor growth in vivo. Mutation of serine 897 to alanine completely abolished growth of one line of GSC cells derived from a mouse. Similarly, the growth of PC-3 human prostate cancer cell xenograft was also dramatically retarded when S897A mutant ephA2 was expressed. FIG. 19 shows Akt-mediated phosphorylation of S897 of EphA2 is required for tumor xeno graft in vivo. A) PC3 human prostate cancer cells were stably infected with retroviral vectors expressing wild type or S897A mutant EphA2. The cells were then implanted subcutaneously into the hind flanks of 6 weeks old nude mice and tumor growth monitored by a digital caliper. B) A mouse glioma stem cell (GSC) line with Ink4 and PTEN double knockout were similarly infected with wild type or S897 mutant EphA2 and injected subcutaneously. Note that GSC cells expressing S897A-EphA2 completely failed to grow in vivo. PC3 cells expressing S897A-EphA2 also displayed significantly reduced growth rate compared with cells expressing wild type EphA2.

Materials and Methods

Reagents

EphrinA1-Fc was produced as described (Miao et al., 2000). Fc fragment of human IgG and fluorescence conjugated secondary antibodies were purchased from Jackson ImmunoResearch. Rabbit polyclonal anti-pS374-Akt, anti-pT308-Akt, anti-Akt, and anti-Akt-pS/T-substrates (Akt-pSub) were obtained from Cell Signaling. Rabbit antip-EphA/B was raised against the conserved phosphopeptides from the juxtamembrane regions. Mouse monoclonal anti-p-ERK1 and rabbit polyclonal anti-EphA2 were purchased from Santa Cruz. D7 mouse monoclonal anti-EphA2 and PP2A was from Upstates, and 1F7 monoclonal anti-EphA2 antibody was a gift from Dr. Andrew Boyd. Mouse monoclonal anti-VASP was purchased from BD Biosciences. Taxes Redconjugated phalloidin was purchased from Molecular Probe. Rabbit polyclonal phospho-S897-specific antibody was raised against phospho-peptide DPRVSIRLP-pS897-TSGSEGVPFR (SEQ ID NO: 1). LY294002, SU5402, FGFR inhibitor (1-(2-Amino-6-(3,5-dimethoxyphenyl)pyrido[2,3-d]pyrimidin-7-yl)-3-tert-butyl urea), and Akt inhibitor II (SH-5) were purchased from Calbiochem.

Constructs

The sequence analysis of EphA2 has revealed multiple serine/threonine sites that resemble the consensus sequence (RXRXXT/S) (Alessi, D. R., Caudwell, F. B., Andjelkovic, M., Hemmings, B. A., and Cohen, P. (1996). Molecular basis for the substrate specificity of protein kinase B; comparison with MAPKAP kinase-1 and p70 S6 kinase. FEBS Lett. 399, 333-338; Cell 129, 1261-1274) for Akt catalytic activity. They include S910, S897, T838, T795, and 5636 in the cytoplasmic domain. 5479 in the extracellular domain of EphA2 that also confirms to the consensus sequence was used a negative control. Single mutation of each of potential serine/threonine residuals to alanine was generated by site-directed mutagenesis using QuickChange Kit (Strategen) following the manufacturer's instruction. The mammalian expression plasmid that contains full length EphA2 sequence (pBabe-EphA2) was used as the template. The reconstructed plasmids were transferred into cells either by transfection using FuGene 6.0 or retroviral infection. For retroviral infection, the plasmids were first transfected into retroviral producing Phoenix cells. The medium collected from the puromycin-selected Phoenix cells was used for cell infection.

EXPRESSION ARREST Lentiviral shRNA system targeting EphA2 was purchased from OpenBiosystems. Viral production and infection were carried out according to manufacturer's instructions.

Cell Culture

Human glioma cell lines U87 and U373 were kindly provided by Dr. L. M. Wang (CCF, Cleveland). LN229 cell line was the gift from Dr. Susann Brady-Kalnay (CWRU, Cleveland). A172 and T98G cells were gifts from Dr. Lee Fortunato. All five cell lines were maintained in Dulbeco's modified MEM medium (DMEM) supplemented with 10% FBS, 10 mg/ml glutamate, 100 U/ml penicillin, and 0.1 mg/ml streptomycin. HEK293 cells were maintained in the same medium. PC3-M cells were maintained in RPMI-1640 supplemented with 10% FBS, 10 mg/ml glutamate, 100 U/ml penicillin, and 0.1 mg/ml streptomycin.

Cell Migration

The chemotactic cell migration was carried out as described previously (J. Cell Biol. 162, 1281-1292). Briefly, both sides of the filter were coated with 10 µg/ml rat tail collagen type I at 4° C. overnight. $1 \times 10^5$ cells in serum-free medium containing 0.1% BSA were plated in the top of insert. EphrinA1-Fc or Fc was added to a final concentration of 1 µg/ml to the lower chamber together 5% FBS or various growth factors. Cells were allowed to migrate for 4 hours and then fixed with 4% paraformaldehyde. After staining with 0.5% crystal violet, cells that have passed through the filter and stayed on the undersides of inserts were counted.

Scratch-Wounding Assay

Scratch-wounding assay was performed as described previously (J. Biol. Chem. 280, 923-932). Cells were plated on 12-well plates for measuring wound closing rate, on coverslips in 24-well plates for immunofluorescence analysis, or on 100 mm dishes for biochemical analyses and grown to confluence. The monolayer of confluent cells was then scratch-wounded with a pipette tip (12- or 24-well plates) or with a multichannel pipette (100 mm dishes).

MatriGel Invasion Assay

The growth factor-reduced MatriGel-coated Transwell inserts (BD Biosciences) were rehydrated with DMEM for 2 hours at 37° C. $2.5 \times 10^4$ cells were plated in the upper chamber. EphrinA1-Fc or Fc was added to the lower chamber containing 5% FBS in DMEM. After incubation at 37° C. for 16-20 hours, cells were fixed and stained with 0.5% crystal violet. Cells migrating through the MatriGel and the pores of the filter were counted from six randomly selected fields.

Cell Stimulation, Immunoprecipitation and Immunoblot

For stationary cells, sub-confluent cells were stimulated with 1 µg/ml ephrinA1-Fc for different times. To study the signaling events in migrating cells, the monolayer of freshly confluent cells was wounded by repeated scratch-wounding using a multichannel pipette. By doing so, the cells on the wound edges were induced to migrate. Four hours after wounding cells were stimulated with 1 µg/ml ephrinA1-Fc for different times. To look at the serum-induced signaling, cells were starved in serum-free medium overnight before stimulation or wounding. Both stationary and wounded cells were stimulated with 10% FBS in the presence of 1 µg/ml Fc or ephrinA1-Fc. Immunoprecipitation and immunoblot were performed as described previously (Nat. Cell Biol. 2, 62-69).

PP2A Assay

Serum-starved U373 cells were stimulated with 10% FBS for 10 min and lysed. Cell lysates were incubated in phosphatase buffer containing 20 mM HEPES pH 7.0, 1 mM Dithiothreitol, 1 mM $MnCl_2$, 0.1 mg/ml BSA, 2 µg/ml leupeptin and aprotinin, and 1 mM PMSF with or without PP2A (0.1 U/reaction) at 30° C. for 20 min. The reaction was terminated by adding sample buffer. Proteins were separated on 4-20% Tris-Glycine gel and analyzed by immunoblot.

Immunofluorescence

Cells were seeded on coverslips in 24-well plates, wounded and stimulated as described in the previous section. Cells were fixed with 4% paraformaldehyde on ice for 10 min. After washing with PBS, cells were blocked with 50 mM $NH_4Cl$ for 10 min and permeabilized with 0.3% NP-40 for 10 min. Cells were then incubated with the indicated primary antibodies and followed by detection with FITC-conjugated donkey anti-rabbit IgG or Rhodamine Red X-conjugated donkey anti-mouse IgG. After intensive washing, the coverslips were mounted using DAPI containing mounting medium (Vector).

Time-Lapse Imaging

Time-lapse imaging was performed as described previously (J. Biol. Chem. 280, 923-932). Briefly, U373 cells that expressed vector, WT-EphA2, or S897-EphA2A were plated at low density on 6-well dishes. After overnight culture in a cell culture incubator at 37° C. with 5% CO2, they were placed in CTI-3700 temperature/CO2 control chamber attached to Leica DM-IRE2 inverted microscope. After 1 hour acclimation, time-lapse images were collected for 9 hour with 15 minutes using a SPOT RT-SE camera (Diagnostic Instrument), all of which is operated from MetaMorph software 6.2r2 (Universal Imaging) with the Mutidimensional Analysis (MDA) package.

Immunohistochemistry

Paraffin sections of human tissues were deparaffinized and rehydrated. Antigens were retrieved by boiling sections in citrate buffer (pH 6.0) for 10 minutes. The endogenous peroxidase was blocked with 3% $H_2O_2$. Sections were blocked with 5% normal goat serum, and incubated with rabbit polyclonal anti-pS897-EphA2 (1:500) or anti-pS473-Akt (1:50) at RT for 1-2 hours. After intensive washing in TBST, sections were detected with biotinylated goat anti-rabbit secondary antibody for 30 minutes followed by amplification with ABC reagents (Vectastain), and visualized with 3,3'-diaminobenzidine. Sections were counterstained with Hematoxylin. To test the binding specificity of the rabbit polyclonal anti-pS897-EphA2, the antibody was preincubated with 100 μM phospho-S897 peptide or unphosphorylated S897 peptide at RT for 1 hour. IHC staining was performed using untreated or peptides-treated anti-pS897-EphA2 antibodies. A negative control was obtained by omitting primary antibody.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A method of detecting malignant progression of cancer cells in an animal comprising;
    obtaining a sample of cancer cells from the animal, wherein the cancer cells are selected from astrocytoma or prostate cancer cells;
    determining a level of S897-EphA2 phosphorylation in the cancer cells of the sample;
    comparing the determined level of S897-EphA2 phosphorylation in the sample to a control value; and
    identifying malignant progression of the cancer cells in the subject where the level of S897-EphA2 phosphorylation is increased compared to the control value.

2. The method of claim 1, the level of S897-EphA2 phosphorylation in the sample being determined by an immunoassay.

3. The method of claim 2, the immunoassay including an antibody specifically binds to the S897-EphA2 phosphorylation site.

4. The method of claim 1, wherein the animal is a human.

5. The method of claim 1, wherein an increase of at least about 20% in the determined level of S897-EphA2 phosphorylation compared to the control value characterizes the cancer cells as being malignant.

6. The method of claim 1, wherein an increase of at least about 50% in the determined level of S897-EphA2 phosphorylation compared to the control value characterizes the cancer cells as being malignant.

7. The method of claim 3, wherein the antibody specifically binds to an amino acid sequence comprising SEQ ID NO: 1.

* * * * *